US010435712B2

(12) United States Patent
Rose et al.

(10) Patent No.: US 10,435,712 B2
(45) Date of Patent: *Oct. 8, 2019

(54) EVOLUTION OF HIGH-TITER VIRUS-LIKE VESICLES FOR VACCINE APPLICATIONS

(71) Applicant: YALE UNIVERSITY, New Haven, CT (US)

(72) Inventors: John Rose, Guilford, CT (US); Nina Rose, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/305,237

(22) PCT Filed: May 11, 2015

(86) PCT No.: PCT/US2015/030102
§ 371 (c)(1),
(2) Date: Oct. 19, 2016

(87) PCT Pub. No.: WO2015/175382
PCT Pub. Date: Nov. 19, 2015

(65) Prior Publication Data
US 2017/0051307 A1    Feb. 23, 2017

Related U.S. Application Data

(60) Provisional application No. 61/994,161, filed on May 16, 2014.

(51) Int. Cl.
*C12N 15/86* (2006.01)
*A61K 39/00* (2006.01)

(52) U.S. Cl.
CPC .............. *C12N 15/86* (2013.01); *A61K 39/00* (2013.01); *A61K 2039/5256* (2013.01); *A61K 2039/5258* (2013.01); *A61K 2039/545* (2013.01); *A61K 2039/57* (2013.01); *C12N 2760/20245* (2013.01); *C12N 2770/36122* (2013.01); *C12N 2770/36134* (2013.01); *C12N 2770/36151* (2013.01); *C12N 2810/6081* (2013.01); *C12N 2840/20* (2013.01)

(58) Field of Classification Search
None
See application file for complete search history.

(56) References Cited

U.S. PATENT DOCUMENTS

| 2003/0099932 | A1 | 5/2003 | Lorens et al. | |
|---|---|---|---|---|
| 2005/0064024 | A1 | 3/2005 | Vadrucci et al. | |
| 2010/0322965 | A1* | 12/2010 | Rose | A61K 39/205 424/204.1 |
| 2011/0223197 | A1 | 9/2011 | Vajdy et al. | |

FOREIGN PATENT DOCUMENTS

WO    2015175382 A1    11/2015

OTHER PUBLICATIONS

Smerdou et al. Two-Helper RNA System for Production of Recombinant Semliki Forest Virus Particles. J. of Virol. 73(2): 1092-1098.*
Del Vecchio et al. Analysis of human immunodeficiency virus type 1 vector cis- and trans-acting elements production by means of Semliki Forest virus. Gene Therapy (2009) 16, 279-290.*
Ehrengruber et al. Semliki Forest virus vectors with mutations in the nonstructural protein 2 gene permit extended superinfection of neuronal and non-neuronal cells. Journal of NeuroVirology, 13: 353-363, 2007.*
Rodriguez-Madoz et al. Semliki Forest Virus Vectors Engineered to Express Higher IL-12 Levels Induce Efficient Elimination of Murine Colon Adenocarcinomas. Molecular Therapy, 2005, 12: 153-163.*
GenBank: EF535150.1. Semliki Forest virus expression vector pSFV4(PD), complete sequence. Dated Sep. 24, 2007.*
Osborn et al. A Picornaviral 2A-Like Sequence-Based Tricistronic Vector Allowing for High-Level Therapeutic Gene Expression Coupled to a Dual-Reporter System. Molecular Therapy, 2005, 12: 569-574.*
Extended European Search Report for European Patent Application No. 15793517.2 dated Nov. 24, 2017.
International Search Report and Written Opinion for PCT International Application No. PCT/US2015/030102 dated Aug. 17, 2015.
Nayak, et al., "Progress and prospects: immune responses to viral vectors", Gene Ther. 17(3), 2010, 295-304.
Novella, et al., "Positive selection of synonymous mutations in vesicular stomatitis virus", J Mol Biol. 342(5), 2004, 1415-1421.
Rolls, et al., "Expression of additional genes in a vector derived from a minimal RNA virus", Virology 218(2), 1996, 406-411.
Rolls, et al., "Novel infectious particles generated by expression of the vesicular stomatitis virus glycoprotein from a self-replicating RNA", Cell 79(3), 1994, 497-506.
Rose, et al., "Hybrid alphavirus-rhabdovirus propagating replicon particles are versatile and potent vaccine vectors", Proc Natl Acad Sci U S A. 105(15), 2008, 5839-5843.
Schell, et al., "Significant protection against high-dose simian immunodeficiency virus challenge conferred by a new prime-boost vaccine regimen", J Virol. 85(12), 2011, 5764-5772.
Spuul, et al., "Phosphatidylinositol 3-kinase-, actin-, and microtubule-dependent transport of Semliki Forest Virus replication complexes from the plasma membrane to modified lysosomes", J Virol. 84(15), 2010, 7543-7557.

* cited by examiner

*Primary Examiner* — Nianxiang Zou
(74) *Attorney, Agent, or Firm* — Saul Ewing Arnstein & Lehr LLP; Kathryn Doyle; Debora Plehn-Dujowich

(57) ABSTRACT

The present invention relates to the discovery of a high titer hybrid-virus vector that gives rise to high titer virus like vesicles (VLVs) that can be used as a vaccine. The invention includes compositions and methods of generating an evolved hybrid-virus vector vaccine and selecting high titer VLVs, methods of treating and/or preventing or immunizing against, a specific disease or disorder, and methods of inducing a memory T cell and B cell immune response in a subject administered the VLV composition produced thereby. Furthermore, the invention encompasses a pharmaceutical composition for vaccinating a subject as well as a high titer protein expression system.

43 Claims, 11 Drawing Sheets

Figure 1A:
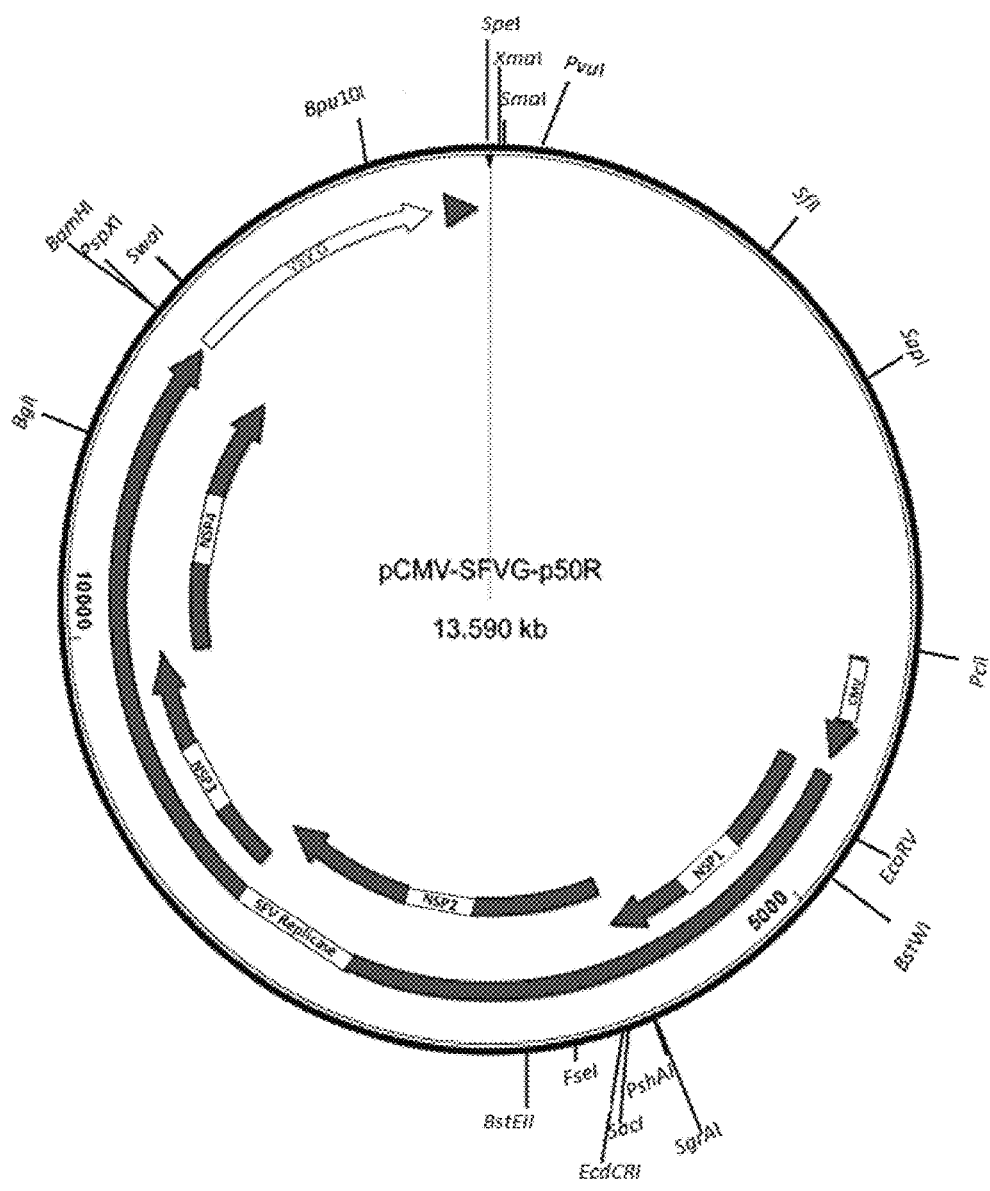

Specification includes a Sequence Listing.

A

B

A

Plasma membrane

Spherules containing SFV replicons form at the plasma membrane and are rapidly endocytosed to form CPVs

CPV nsP1-4 replication complex

B

VSV G

Endocytosis of spherules is inhibited when the replicons express VSV G protein. Infectious VLVs are released inefficiently from cells.

C

Passaged VLVs evolved mutations in SFV nsPs including a PTAP late domain motif that promotes efficient budding.

FIGS. 9A-9C

EVOLUTION OF HIGH-TITER VIRUS-LIKE VESICLES FOR VACCINE APPLICATIONS

CROSS-REFERENCE TO RELATED APPLICATIONS

The present application is a 35 U.S.C. § 371 national phase application from, and claims priority to, International Application No. PCT/US2015/030102, filed May 11, 2015, and published under PCT Article 21(2) in English, which claims priority under 35 U.S.C. § 119(e) to U.S. Provisional Application No. 61/994,161, filed May 16, 2014, all of which applications are incorporated herein by reference in their entireties.

STATEMENT REGARDING FEDERALLY SPONSORED RESEARCH OR DEVELOPMENT

This invention was made with government support under grants R37 AI040357 and RO1 AI45510, awarded by National Institute of Health. The government has certain rights in the invention.

BACKGROUND OF THE INVENTION

Vaccination is one of the greatest public health success stories. Nowadays vaccines that protect against many of the viruses that once caused fatal childhood diseases are routinely used throughout the world. However, traditional methods of vaccine development using inactivation or attenuation of viruses have failed for some of the most deadly human pathogens, necessitating new approaches. Advances in molecular virology have enabled the genetic manipulation of viruses, which has opened new opportunities for vaccine development. Genetic modification of viruses not only allows for their attenuation but also for incorporation of sequences from other viruses, turning one pathogen into a vaccine carrier for another. Viral vectors have been studied as potential tools to deliver vaccines as they present advantages over traditional vaccines in that they stimulate a broad range of immune responses including antibody (B cell), T helper cell (CD4+ T cell), and cytotoxic T lymphocyte (CTL, CD8+ T cell) mediated immunity. These viral vector vaccines could be used against various infectious and malignant diseases (Polo and Dubensky, Jr. Drug Discov Today. 2002, Jul. 1; 7(13):719-27; Small and Hildegund, Curr Opin Virol. 2011, Oct. 1; 1(4): 241-245). However, there are limitations on the use of viral vector-based vaccines. For example, preexisting anti-vector immunity against the viral vectors that potentially inactivate the vaccine presents an issue as does the limited cloning capacity for the transgene of interest. Numerous vaccine investigations are in progress to improve the efficiency of this technology and to overcome its limitations (Nayak and Herzog. Gene Therapy, 2009, 17 (3): 295-304).

Enveloped RNA viruses have highly organized structures. One or more nucleocapsid proteins encapsidate their RNA, matrix proteins often lie between the capsid and the membrane, and one or more transmembrane glycoproteins interact with the matrix or nucleocapsid proteins to direct efficient particle assembly. Once the particles are released from cells, one or more glycoproteins bind cellular receptors and catalyze membrane fusion to allow the viruses to enter new cells.

Alphaviruses such as Semliki Forest Virus (SFV) are positive-strand, membrane-enveloped RNA viruses that encode four non-structural proteins called nsP 1-4 and three structural proteins: capsid, and the E1 and E2 transmembrane glycoproteins. The nsp 1-4 proteins are translated from the first two-thirds of the genomic RNA. These proteins form a complex which directs replication of the genomic RNA to form antigenomic RNA, which is then copied to form full-length positive strand RNA and a subgenomic mRNA that encodes the structural proteins. The capsid protein encases the genomic RNA in the cytoplasm to generate a nucleocapsid that buds from the cell surface in a membrane containing the SFV glycoproteins. Alphavirus RNA replication occurs inside light-bulb shaped, membrane-bound compartments called spherules that initially form on the cell surface and are then endocytosed to form cytopathic vacuoles containing multiple spherules (Spuul et al., 2010. Journal of virology 84:7543-7557). The replicase proteins are localized to the cytoplasmic side of the spherules (Froshauer et al., 1988. The Journal of cell biology 107:2075-2086). How the replicated RNA in the spherules is packaged into nucleocapsids prior to SFV budding is not known. Alphavirus RNA replicons lacking any structural protein genes can still replicate efficiently inside a cell, but they are incapable of propagating beyond the cell.

Vesicular stomatitis virus (VSV) is a negative-strand RNA virus that encodes a single membrane glycoprotein (G), a matrix protein, and a nucleocapsid protein as well as two proteins that form the viral polymerase (Rose and Whitt, 2001. *Rhabdoviridae*: The Viruses and Their Replication, p. 1221-1240. In D. Knipe and P. Howley (ed.), Fields' Virology. Lippencott-Raven, Philadelphia). Remarkably, when cells are transfected with an SFV RNA replicon encoding only the SFV non-structural proteins and the VSV G protein, infectious membrane-enveloped vesicles containing the VSV G protein are generated (Rolls et al., 1994. Cell 79:497-506). These infectious, virus-like vesicles (VLVs) grow to low titers, but can be passaged like a virus in tissue culture cells. The particles contain the replicon RNA and VSV G protein, but unlike enveloped RNA viruses, have a very low density because they do not contain a tightly-packed nucleocapsid protein around the RNA (Rolls et al., 1994. Cell 79:497-506). The mechanism by which these VLVs are generated has not been determined. These VLVs expressing other proteins have proven useful as experimental vaccines (Rose et al., 2008. PNAS 105:5839-5843; Schell et al., 2011. Journal of virology 85:5764-5772). But, there are two significant limitations of the VLV system as a vaccine platform: the relatively low titer of the VLVs and rapid loss of expression of the foreign genes upon passage.

Clearly, there is a need in the art for methods of producing more efficient virus-vector vaccine systems that support stable foreign gene expression, while generating high vaccine titers that induce a potent immune response. The present invention fulfills this need.

BRIEF SUMMARY OF THE INVENTION

The present invention provides compositions and methods of use of a high titer hybrid-virus vector comprising a DNA sequence comprising a promoter sequence operably linked to a DNA sequence encoding alphavirus non-structural protein nucleotide sequences, operably linked to an alphavirus subgenomic RNA promoter, operably linked to a 2A DNA encoding a 2A peptide, which is in turn operably linked to a vesicular stomatitis virus (VSV) G DNA encoding a VSV G protein. The alphavirus non-structural protein nucleotide sequences of the high titer hybrid-virus vector of the invention comprise at least two of the mutations selected from the group consisting of G-4700-A, A-5424-G, G-5434-

A, T-5825-C, T-5930-C, A-6047-G, G-6783-A, G-6963-A, G-7834-A, T-8859-A, T-8864-C, G-9211-A, A-10427-G, G-11560-A, A-11871-G and T-11978-C and the vector of this invention lacks functional nucleotide sequences which encode alphavirus structural proteins. Furthermore, when the vector of the present invention is propagated in cell culture, titers of at least $10^7$ plaque forming units (pfu) per ml of virus like vesicles (VLVs) are obtained.

In another aspect, the invention includes a protein expression system including a high titer hybrid-virus vector comprising a DNA sequence comprising a promoter sequence operably linked to a DNA sequence encoding alphavirus non-structural protein nucleotide sequences, operably linked to an alphavirus subgenomic RNA promoter, operably linked to a 2A DNA encoding a 2A peptide, which is in turn operably linked to a vesicular stomatitis virus (VSV) G DNA encoding a VSV G protein, wherein the alphavirus non-structural protein sequences comprise at least two of the mutations selected from the group consisting of G-4700-A, A-5424-G, G-5434-A, T-5825-C, T-5930-C, A-6047-G, G-6783-A, G-6963-A, G-7834-A, T-8859-A, T-8864-C, G-9211-A, A-10427-G, G-11560-A, A-11871-G and T-11978-C, wherein the vector lacks functional nucleotide sequences which encode alphavirus structural proteins, further wherein when the vector is propagated in cell culture, titers of at least $10^7$ plaque forming units (pfu) per ml of virus like vesicles (VLVs) are obtained.

The invention also includes a method of stabilizing the expression of a VSV G protein in VLVs. The method comprises operably linking a 2A DNA encoding a 2A peptide to DNA encoding a VSV G protein such that expression of the VLV G protein is maintained throughout replication of the VLVs.

The invention further includes a method of stabilizing the expression of a heterologous protein in VLVs. The method comprises operably linking a 2A DNA encoding a 2A peptide to DNA encoding a heterologous protein, in turn operably linked to a VSV G protein such that expression of the heterologous protein is maintained throughout replication of the VLVs.

In some embodiments, the alphavirus is Semliki Forest virus (SFV). In other embodiments, the subgenomic RNA promoter is an Semliki Forest virus (SFV) promoter.

In some embodiments, the 2A DNA is Thosea asigna virus DNA and encodes a T2A peptide. In some embodiments, the high titer hybrid-virus vector generates Virus like vesicles (VLVs) containing a replicon RNA. In some embodiments, the promoter sequence of high titer hybrid-virus vector is a constitutive promoter. In other embodiments, the promoter sequence is the cytomegalovirus immediate early promoter. In some embodiments, titers of at least $5\times10^7$ pfu/ml of VLVs are obtained. In other embodiments, titers of at least $1\times10^8$ pfu/ml of VLVs are obtained. In some embodiments, a DNA encoding at least one heterologous protein is inserted between the SFV subgenomic RNA promoter, and the 2A DNA of the high titer hybrid-virus vector.

In another aspect, the invention provides a composition comprising virus like vesicles (VLVs) produced by the high titer hybrid-virus vector of this invention.

In some embodiments, a composition comprising virus like vesicles (VLVs) is produced by the high titer hybrid-virus vector of this invention wherein a DNA encoding at least one heterologous protein is inserted between the SFV subgenomic RNA promoter, and the 2A DNA.

In another aspect, the invention includes a method of immunizing a subject against a heterologous protein. The method comprises administering to the subject a composition comprising at least $10^7$ pfu/ml of the VLVs produced by the high titer hybrid-virus vector of this invention wherein a DNA encoding at least one heterologous protein is inserted between the SFV subgenomic RNA promoter, and the 2A DNA, wherein expression of the heterologous protein induces an immune response in the subject.

The invention also includes a method of treating and/or preventing a disease in a subject. The method comprises administering to a subject in need of such treatment a therapeutically effective amount of the virus like vesicles (VLVs) composition produced by the high titer hybrid-virus vector of this invention wherein a DNA encoding at least one heterologous protein is inserted between the SFV subgenomic RNA promoter, and the 2A DNA. In other embodiments, the disease selected from the group consisting of infectious disease, malignant disease and autoimmune disease.

The present invention also provides a method of vaccinating a subject wherein administration of the composition elicits an immune response in the subject. The method of vaccination comprises administering to the subject a pharmaceutically acceptable amount of the composition of the virus like vesicles (VLVs) composition produced by the high titer hybrid-virus vector of this invention wherein a DNA encoding at least one heterologous protein is inserted between the SFV subgenomic RNA promoter, and the 2A DNA.

In some embodiments, the composition that elicits an immune response in the subject is administered prophylactically. In other embodiments, the composition is administered therapeutically to the subject. In further embodiments, the composition is administered in combination with an adjuvant. In yet further embodiments, the adjuvant is selected from the group consisting of Freund's complete adjuvant, Freund's incomplete adjuvant, Quil A, Detox, ISCOMs and squalene.

In another aspect, the invention includes a method of generating a memory T cell immune response to a heterologous protein in a subject. The method comprises the steps of administering to a subject, in an amount effective to elicit an immune response in the subject, the VLVs composition produced by the high titer hybrid-virus vector of this invention wherein a DNA encoding at least one heterologous protein is inserted between the SFV subgenomic RNA promoter, and the 2A DNA and administering at a second, subsequent time period, a second effective amount of the previous VLVs composition, wherein T memory cells directed against the heterologous protein are generated in the subject.

The invention also includes a method of generating an adaptive B cell immune response to a heterologous protein in a subject. The method comprises the steps of administering to a subject, in an amount effective to elicit an immune response in the subject, the VLVs composition produced by the high titer hybrid-virus vector of this invention wherein a DNA encoding at least one heterologous protein is inserted between the SFV subgenomic RNA promoter, and the 2A DNA and administering at a second, subsequent time period, a second effective amount of the previous VLVs composition, wherein B memory cells directed against the heterologous protein are generated in the subject.

In some embodiments, the heterologous protein is associated with a disease selected from the group consisting of infectious disease, malignant disease and autoimmune disease. In further embodiments, the infectious disease is caused by a prokaryote selected from the group consisting of *Escherichia, Streptococcus, Staphylococcus, Bordetella,*

Corynebacterium, Mycobacterium, Neisseria, Haemophilus, Actinomycetes, Streptomycetes, Nocardia, Enterobacter, Yersinia, Fancisella, Pasteurella, Moraxella, Acinetobacter, Erysipelothrix, Branhamella, Actinobacillus, Streptobacillus, Listeria, Calymmatobacterium, Brucella, Bacillus, Clostridium, Treponema, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Coxiella, Borrelia and Mycoplasma. In yet further embodiments, the infectious disease is caused by a virus selected from the group consisting of human immunodeficiency virus (HIV), hepatitis A virus (HAV), hepatitis B (HBV), hepatitis C (HCV), any other hepatitis-associated virus, human papillomavirus (HPV) and especially high-risk oncogenic human papillomavirus types, Kaposi's Sarcoma-Associated Herpesvirus (KSHV) (also known as Human Herpesvirus-8 (HHV-8)), Herpes Simplex virus (HSV) (any subtype), Respiratory Syncytial Virus (RSV) and associated respiratory viruses, Influenza viruses, coronaviruses including SARS-associated Coronavirus (SARS-CoV), rhinovirus, adenovirus, SIV, rotavirus, human papilloma virus, arbovirus, measles virus, polio virus, rubella virus, mumps virus, papova virus, cytomegalovirus, varicella-zoster virus, varicella virus, huntavirus and any emergent virus, in particular Ebola virus, Marburg virus, West Nile virus (WNV), St Louis Encephalitis virus (SLEV), Rift Valley Fever virus (RVFV) and other members of the Bunyaviridae. In yet further embodiments, the infectious disease is caused by a protozoan selected from the group consisting of apicomplexans and trypanosomatids. In yet further embodiments, the malignant disease is a cancer selected from the group consisting of Acute and Chronic Myelogenous Leukemia (AML, CML), Follicular Non-Hodgkins lymphoma, malignant melanoma, Hairy Cell leukaemia, multiple myeloma, carcinoid tumors with carcinoid syndrome and liver and lymph node metastases, AIDS related Kaposi's sarcoma, renal cell carcinoma, adenocarcinoma of the large bowel, squamous cell carcinoma of the head and neck, colon cancer, lung cancer, breast cancer, stomach cancer, prostate cancer, and endometrial cancer. In yet other embodiments, the autoimmune disease is selected from the group consisting of Addison's disease, Celiac disease, Dermatomyositis, Graves' disease, Hashimoto's thyroiditis, Multiple sclerosis, Myasthenia gravis, Pernicious anemia, Reactive arthritis, Rheumatoid arthritis, Sjogren syndrome, Systemic lupus erythematosus and Type I diabetes.

In another aspect, the invention includes a method of selecting high titer RNA virus like vesicles (VLVs). The method comprises generating VLVs by passaging in a cell culture a hybrid-virus vector comprising an RNA sequence encoding a viral structural protein, wherein the viral structural protein does not comprise an alphavirus structural protein, and screening the generated VLVs for high titer VLVs using at least one procedure selected from the group consisting of extensive passaging of VLVs in cell culture and direct mutagenesis of the VLVs.

In some embodiments, the hybrid-virus vector RNA sequence encodes an alphavirus non-structural protein. In some embodiments, the non-structural protein is a Semliki Forest virus (SFV) non-structural protein. In other embodiments, the viral structural protein comprises a rhabdovirus glycoprotein. In other embodiments, the glycoprotein is vesicular stomatitis virus (VSV) G protein. In further embodiments, the high titer VLVs produce at least $10^7$ plaque forming units (pfu) per ml. In yet further embodiments, the high titer VLVs are administered to a subject in an effective amount to induce an immune response.

In some embodiments, the subject is a mammal. In other embodiments, the mammal is a human.

In a further aspect, the invention includes an RNA virus like vesicle (VLV), having a titer of at least $10^7$ plaque forming units (pfu). The RNA VLV of this invention lacks SFV structural proteins nucleotide sequences and comprises VSV G protein nucleotide sequences and SFV non-structural protein nucleotide sequences comprising at least two of the mutations selected from the group consisting of G-4700-A, A-5424-G, G-5434-A, T-5825-C, T-5930-C, A-6047-G, G-6783-A, G-6963-A, G-7834-A, T-8859-A, T-8864-C, G-9211-A, A-10427-G, G-11560-A, A-11871-G and T-11978-C.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1B are series of diagrams illustrating the VLV DNA construct. FIG. 1A:Map of the p50 RNA genome reconstructed into a DNA vector with the CMV promoter: pCMV-SFVG-p50R. FIG. 1B illustrates a deletion and eleven amino acid changes in high-titer evolved VLVs.

FIG. 2 is an image showing that the VSV G is the structural protein in p50 VLVs.

FIGS. 3A-3D are series of images illustrating electron micrographs of p50 VLVs. FIGS. 3A-3B: Many of the particles appear to have protein spikes, presumably VSV G protein, on their surfaces (arrows). FIG. 3C: Some of the particles prepared for TEM by this method also appear to be broken and releasing nucleic acid. FIG. 3D: TEM on particles that were unfixed, and labeled with antibody to VSV G followed by a secondary antibody conjugated to 12 nm gold particles. The particles were then negative-stained with phosphotungstic acid.

FIGS. 4A-4B are series of graphs and images depicting the growth of p50 VLVs compared with VSV. FIG. 4A: Growth curve of p50 VLVs compared with VSV displaying number of pfu/ml post infection. FIG. 4B: Plates showing that plaque size of the VLV titers were about 8-10 fold lower than VSV.

FIG. 5 is a diagram depicting the reconstruction of the p50 VLV genome in the DNA-launched vector (pCMVSFVG-p50R).

FIGS. 6A-6E are series of images illustrating thin-section electron micrographs of cells infected with VLVs. TEM of fixed, thin sections of cells at seven hours after infection. FIGS. 6A-6B: The plasma membranes of cells infected with the low titer VLVs showed numerous spherical structures that often appear to be attached to the cell surface by a thin "neck" (white arrows). FIG. 6C: intracellular vacuoles that are typical CPVs containing SFV spherules attached by a neck to the membrane (white arrows). FIGS. 6D-6E: low titer VLVs, cells infected with the p50 VLVs showed only occasional vesicles that appear to be budding from the cell surface. These also appear in many cases to be connected by a neck-like structure (white arrows).

FIG. 7 is a graph demonstrating that the PTAP motif is required for high-titer VLV production.

FIGS. 8A-8B are series of diagrams and images depicting the expression of SIV Gag and VSV G from a single mRNA in the high-titer VLVs. FIG. 8A: Illustration of the VLV gene map. FIG. 8B: SDS-PAGE and western blotting with antibody to SIV Gag and VSV G. Expression of both Gag and G from cells infected with the VLVs was verified.

FIGS. 9A-9C are a series of images illustrating the model for generation of high-titer VLVs. FIG. 9A: Spherules containing SFV replicons are normally transported to the cell surface and then rapidly endocytosed. FIG. 9B: Endocytosis of SFV replicons expressing VSV G is inhibited by VSV G. Inefficient release of infectious VLVs. FIG. 9C: Passaged VLVs evolved PTAP sequence in nsP1 and additional mutations allowing efficient budding using cellular ESCRT machinery.

Figure 10:
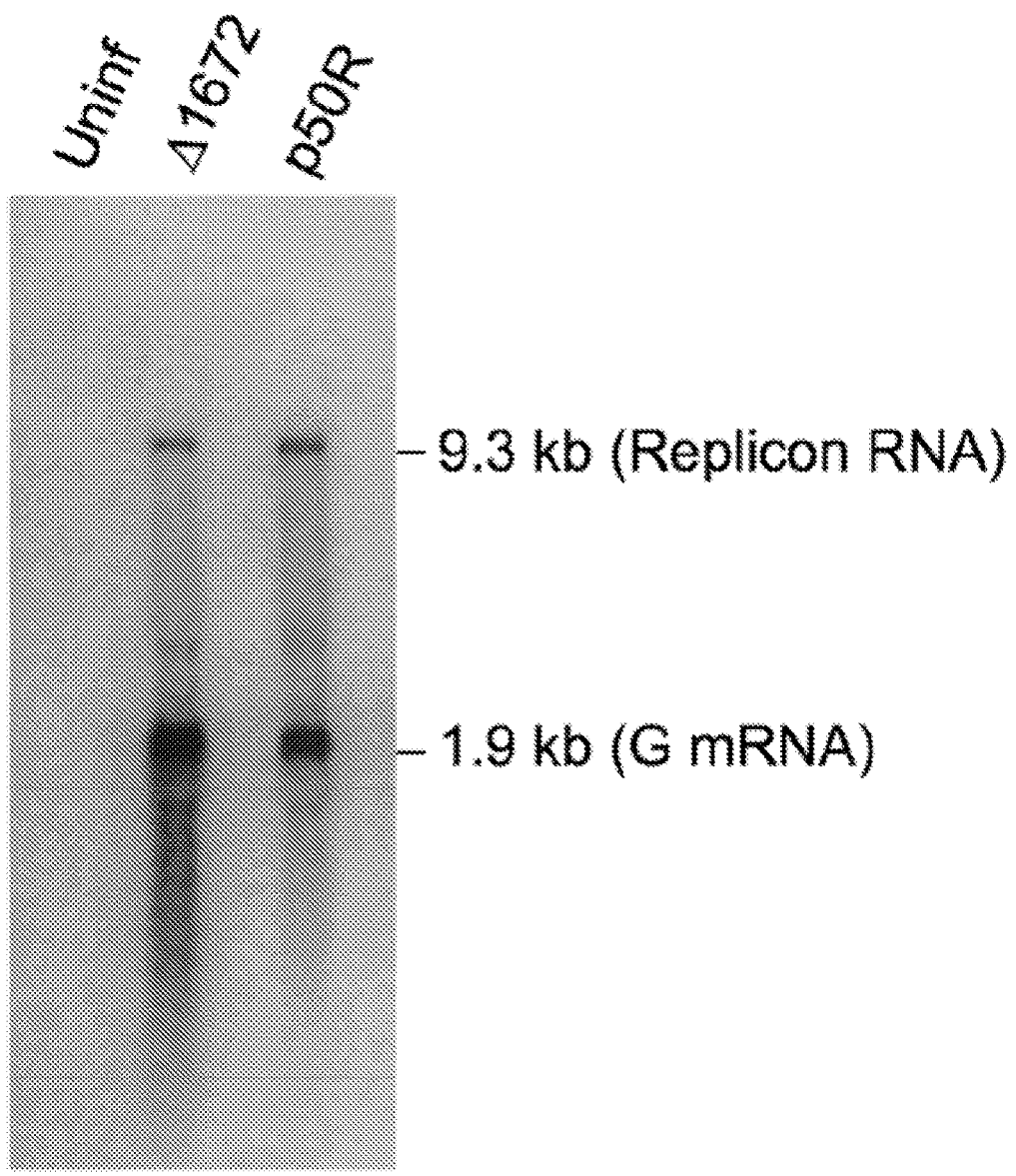

FIG. 10 is an image representing northern blot analysis of genomic and subgenomic G mRNA. The blot shows the position of the 9.2-kb genomic replicon RNA and the subgenomic 1.9-kb VSV G protein (VSVG) mRNA expressed in cells infected with VLVs derived from cells transfected with pCMV-SFVG-Δ1672 or pCMV-SFVG-p50R. Lane of RNA from uninfected cells is labeled UNIF.

DETAILED DESCRIPTION OF THE INVENTION

The present invention relates to the unexpected discovery that evolved virus like particles (VLVs) can grow to much higher titers (1000-fold or more) and can express foreign genes more stable than the previously described VLVs particles (U.S. application Ser. No. 12/747,59; Rolls et al., 1994. Cell 79:497-506 and Rolls et al., 1996. Virology 218:406-41). Thus, in various embodiments described herein, there are disclosed compositions and methods that relate to the generation of an evolved hybrid-virus vector vaccine comprising DNA encoding mutated alphavirus nonstructural protein nucleotide sequences, mutated non-alphavirus structural nucleotide sequences and a eukaryotic promoter, wherein the evolved hybrid-virus vector vaccine produces high titer VLVs. Additionally, the current invention includes compositions and methods of selecting VLVs, methods of treating and/or preventing or immunizing against, a specific disease or disorder, and methods of inducing a memory T and B cell immune response in a subject administered the VLVs of the invention.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, "greater" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween, than a control.

As used herein, the terms "control," or "reference" are used interchangeably, and refer to a value that is used as a standard of comparison.

A "subject" or "patient," as used therein, may be a human or non-human mammal. Non-human mammals include, for example, livestock and pets, such as ovine, bovine, porcine, canine, feline and murine mammals. Preferably, the subject is human.

A "mutation" as used therein is a change in a DNA sequence resulting in an alteration from its natural state. The mutation can comprise a deletion and/or insertion and/or duplication and/or substitution of at least one desoxyribonucleic acid base such as a purine (adenine and/or thymine) and/or a pyrimidine (guanine and/or cytosine). Mutations may or may not produce discernible changes in the observable characteristics (phenotype) of an organism.

The term "evolved" or "evolve" as used herein refers to the change (i.e. the evolution) in the inherited characteristics of biological populations over successive generations. Evolutionary processes give rise to diversity at every level of biological organization, including species, individual organisms and molecules such as DNA and proteins (Hall and Hallgrímsson, eds. 2008, Strickberger's Evolution (4th ed.), Jones & Bartlett). In the context of the present invention, the "evolved" hybrid-virus accumulated beneficiary mutations and produced VLVs with 1000 times higher titers after 50 passages in culture than the original hybrid virus.

"Vaccination" refers to the process of inoculating a subject with an antigen to elicit an immune response in the subject, that helps to prevent or treat the disease or disorder the antigen is connected with. The term "immunization" is used interchangeably herein with vaccination.

The term "immunogenicity" as used herein, refers to the innate ability of an antigen or organism to elicit an immune response in an animal when the antigen or organism is administered to the animal. Thus, "enhancing the immunogenicity" refers to increasing the ability of an antigen or organism to elicit an immune response in an animal when the antigen or organism is administered to an animal. The increased ability of an antigen or organism to elicit an immune response can be measured by, among other things, a greater number of antibodies that bind to an antigen or organism, a greater diversity of antibodies to an antigen or organism, a greater number of T-cells specific for an antigen or organism, a greater cytotoxic or helper T-cell response to an antigen or organism, a greater expression of cytokines in response to an antigen, and the like.

The term "activation", as used herein, refers to the state of a cell following sufficient cell surface moiety ligation to induce a noticeable biochemical or morphological change. Within the context of T cells, such activation refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physico-chemical process.

The term "activated T cell" means a T cell that is currently undergoing cell division, cytokine production, performance of regulatory or cytolytic effector functions, and/or has recently undergone the process of "activation."

"Humoral immunity" or "humoral immune response" both refer to B-cell mediated immunity and are mediated by highly specific antibodies, produced and secreted by B-lymphocytes (B-cells).

"Prevention" refers to the use of a pharmaceutical compositions for the vaccination against a disorder.

"Adjuvant" refers to a substance that is capable of potentiating the immunogenicity of an antigen. Adjuvants can be one substance or a mixture of substances and function by acting directly on the immune system or by providing a slow release of an antigen. Examples of adjuvants are aluminium salts, polyanions, bacterial glycopeptides and slow release agents as Freund's incomplete.

"Delivery vehicle" refers to a composition that helps to target the antigen to specific cells and to facilitate the effective recognition of an antigen by the immune system. The best-known delivery vehicles are liposomes, virosomes, microparticles including microspheres and nanospheres, polymeres, bacterial ghosts, bacterial polysaccharides, attenuated bacterias, virus like particles, attenuated viruses and ISCOMS.

"Incorporated into" or "encapsulated in" refers to an antigenic peptide that is within a delivery vehicle, such as microparticles, bacterial ghosts, attenuated bacteria, virus like particles, attenuated viruses, ISCOMs, liposomes and preferably virosomes.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "fusion protein" as used herein refers to a protein wherein the protein comprises two or more proteins linked together by peptide bonds or other chemical bonds.

The proteins can be linked together directly by a peptide or other chemical bond, or with one or more amino acids between the two or more proteins, referred to herein as a spacer.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "RNA" as used herein is defined as ribonucleic acid.

"Transform", "transforming", and "transformation" is used herein to refer to a process of introducing an isolated nucleic acid into the interior of an organism.

The term "treatment" as used within the context of the present invention is meant to include therapeutic treatment as well as prophylactic, or suppressive measures for the disease or disorder. As used herein, the term "treatment" and associated terms such as "treat" and "treating" means the reduction of the progression, severity and/or duration of a disease condition or at least one symptom thereof. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

The term "biological" or "biological sample" refers to a sample obtained from an organism or from components (e.g., cells) of an organism. The sample may be of any biological tissue or fluid. Frequently the sample will be a "clinical sample" which is a sample derived from a patient. Such samples include, but are not limited to, bone marrow, cardiac tissue, sputum, blood, lymphatic fluid, blood cells (e.g., white cells), tissue or fine needle biopsy samples, urine, peritoneal fluid, and pleural fluid, or cells therefrom. Biological samples may also include sections of tissues such as frozen sections taken for histological purposes.

The term "equivalent," when used in reference to nucleotide sequences, is understood to refer to nucleotide sequences encoding functionally equivalent polypeptides. Equivalent nucleotide sequences will include sequences that differ by one or more nucleotide substitutions, additions- or deletions, such as allelic variants; and will, therefore, include sequences that differ from the nucleotide sequence of the nucleic acids described herein due to the degeneracy of the genetic code.

"Hybridization" refers to any process by which a strand of nucleic acid binds with a complementary strand through base pairing. Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. Hybridization also includes the formation of duplexes which contain certain mismatches, provided that the two strands are still forming a double stranded helix. "Stringent hybridization conditions" refers to hybridization conditions resulting in essentially specific hybridization. The term "specific hybridization" of a probe to a target site of a template nucleic acid refers to hybridization of the probe predominantly to the target, such that the hybridization signal can be clearly interpreted. As further described herein, such conditions resulting in specific hybridization vary depending on the length of the region of homology, the GC content of the region, the melting temperature "Tm" of the hybrid. Hybridization conditions will thus vary in the salt content, acidity, and temperature of the hybridization solution and the washes.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. An "isolated cell" or "isolated population of cells" is a cell or population of cells that is not present in its natural environment.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The term "variant," when used in the context of a polynucleotide sequence, may encompass a polynucleotide sequence related to that of a gene or the coding sequence thereof. This definition may also include, for example, "allelic," "splice," "species," or "polymorphic" variants. The polypeptides generally will have significant amino acid identity relative to each other. A polymorphic variant is a variation in the polynucleotide sequence of a particular gene between individuals of a given species. Polymorphic variants may encompass "single nucleotide polymorphisms" (SNPs) in which the polynucleotide sequence varies by one base. The presence of SNPs may be indicative of, for example, a certain population, a disease state, or a propensity for a disease state.

The term "ameliorating" or "treating" means that the clinical signs and/or the symptoms associated with a disease are lessened as a result of the actions performed. The signs or symptoms to be monitored will be well known to the skilled clinician.

As used herein, by "combination therapy" is meant that a first agent is administered in conjunction with another agent. "In combination with" or "In conjunction with" refers to administration of one treatment modality in addition to another treatment modality. As such, "in combination with" refers to administration of one treatment modality before, during, or after delivery of the other treatment modality to the individual. Such combinations are considered to be part of a single treatment regimen or regime.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

"Titers" are numerical measures of the concentration of a virus or viral vector compared to a reference sample, where the concentration is determined either by the activity of the virus, or by measuring the number of viruses in a unit volume of buffer. The titer of viral stocks are determined, e.g., by measuring the infectivity of a solution or solutions (typically serial dilutions) of the viruses, e.g., on HeLa cells using the soft agar method (see, Graham & Van Der eb (1973) Virology 52:456-467) or by monitoring resistance conferred to cells, e.g., G418 resistance encoded by the virus or vector, or by quantitating the viruses by UV spectrophotometry (see, Chardonnet & Dales (1970) Virology 40:462-477).

As used herein, the term "pharmaceutical composition" refers to a mixture of at least one compound useful within the invention with other chemical components, such as carriers, stabilizers, diluents, adjuvants, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

The term "antibody" or "Ab" as used herein, refers to a protein, or polypeptide sequence derived from an immunoglobulin molecule which specifically binds to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv) and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). An antibody may be derived from natural sources or from recombinant sources. Antibodies are typically tetramers of immunoglobulin molecules.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Heterologous antigens" used herein to refer to an antigen that is not endogenous to the organism comprising or expressing an antigen. As an example, a virus vaccine vector comprising or expressing a viral or tumor antigen comprises a heterologous antigen. The term "Heterologous protein" as used herein refers to a protein that elicits a beneficial immune response in a subject, irrespective of its source.

As defined herein, an "Alphavirus" is a member of the Group IV Togaviridae family of viruses. Alphaviruses include, but are not limited to Aura virus, Babanki virus, Barmah Forest virus, Bebaru virus, Cabassou virus, Chikungunya virus, Eastern equine encephalitis virus, Everglades virus, Fort Morgan virus, Getah virus, Highlands virus, Kyzylagach virus, Mayaro virus, Me Tri virus, Middelburg virus, Mosso das Pedras virus, Mucambo virus, Ndumu virus, O'nyong'nyong virus, Pixuna virus, Rio Negro virus, Ross River virus, Sagiama virus, Salmon pancreas disease virus, Semliki Forest virus, Sindbis virus, Southern elephant seal virus, Tonate virus, Trocara virus, Una virus, Venezuelan equine encephalitis virus, Western equine encephalitis virus and Whataroa virus.

As defined herein, an "alphavirus non-structural protein" can be selected from the group consisting of nsp1, nsp2, nsp3 and nsp4.

As defined herein, an "alphavirus structural protein" can be selected from the group consisting of an alphavirus capsid protein and at least one spike protein.

The term "specifically binds", "selectively binds" or "binding specificity" refers to the ability of the humanized antibodies or binding compounds of the invention to bind to a target epitope present on VSV with a greater affinity than that which results when bound to a non-target epitope. In certain embodiments, specific binding refers to binding to a target with an affinity that is at least 10, 50, 100, 250, 500, or 1000 times greater than the affinity for a non-target epitope.

As used herein, the term "effective amount" or "therapeutically effective amount" means the amount of the virus like particle generated from vector of the invention which is required to prevent the particular disease condition, or which reduces the severity of and/or ameliorates the disease condition or at least one symptom thereof or condition associated therewith.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. In the present disclosure, the term "vector" includes an autonomously replicating virus.

The terms "2A" or "2A peptide" is a self-processing viral peptide. The 2A peptide can separate different protein coding sequences in a single ORF transcription unit (Ryan et al., 1991, J Gen Virol 72:2727-2732). Initially, the 2A peptide cleavage was thought to be mediated by an autoproteolytic event and 2A peptides were called "self-cleaving peptides." Ultimately, a ribosomal-skip mechanism was proposed, and 2A and 2A-like sequences are now referred to as CHYSELs (cis-acting hydrolase elements) rather than self-cleaving peptides (Donnelly et al., 2001, J Gen Virol 82:1013-1025) Linking proteins with 2A or 2A-like peptide sequences results in cellular expression of multiple, discrete proteins (in essentially equimolar quantities) derived from a single ORF (de Felipe et al., 2006, Trends Biotechnol 24:68-75).

Description

Compositions

The invention is based in part on the discovery of the high titer hybrid-virus vector illustrated in FIG. 1. The vector comprises a DNA sequence comprising a promoter sequence operably linked to a DNA sequence encoding alphavirus non-structural protein nucleotide sequences comprising at least two of the mutations selected from the group consisting of G-4700-A, A-5424-G, G-5434-A, T-5825-C, T-5930-C, A-6047-G, G-6783-A, G-6963-A, G-7834-A, T-8859-A, T-8864-C, G-9211-A, A-10427-G, G-11560-A, A-11871-G and T-11978-C as shown in Table 1. These sequences are operably linked to DNA specifying a second promoter sequence corresponding to the alphavirus subgenomic RNA promoter. This sequence is in turn operably linked to DNA encoding a vesicular stomatitis virus (VSV) G protein. The vector lacks functional nucleotide sequences which encode alphavirus structural proteins. When the vector is propagated in cell culture, high titers of virus like vesicles (VLVs) are obtained, for example, titers of at least $10^7$ plaque forming units (pfu) per ml are obtained.

The invention also includes an RNA virus like vesicle (VLV), having a titer of at least $10^7$ plaque forming units (pfu), that lacks SFV structural proteins nucleotide sequences and that comprises VSV G protein nucleotide sequences and SFV non-structural protein nucleotide sequences. In one aspect the SFV non-structural protein nucleotide sequences comprise at least two of the mutations selected from the group consisting of G-4700-A, A-5424-G, G-5434-A, T-5825-C, T-5930-C, A-6047-G, G-6783-A, G-6963-A, G-7834-A, T-8859-A, T-8864-C, G-9211-A, A-10427-G, G-11560-A, A-11871-G and T-11978-C.

Methods of making the high titer hybrid-virus vector of the invention are described in detail in the Experimental Examples Section herein.

In one aspect the alphavirus is Semliki Forest virus (SFV). In another aspect the subgenomic RNA promoter is an Semliki Forest virus (SFV) promoter.

In one aspect, the VSV encoding the VSV G protein can be from any VSV serotype known in the art. Non-limiting examples of VSV serotypes include the Indiana (IND-VSV) serotype and New Jersey (NJ-VSV) serotype.

In one aspect, although the cytomegalovirus immediate early promoter is exemplified herein, the invention should not be construed to be limited to this promoter sequence. Promoter sequences that are useful in the invention include any promoter that induces high levels of gene expression. Such promoters may include, but are not limited to those disclosed elsewhere herein.

In another aspect of the invention, the hybrid-virus vector may achieve titers of at least $5 \times 10^7$ pfu/ml, at least $1 \times 10^8$ pfu/ml or more when the hybrid-virus vector is propagated in cell culture.

In a further aspect of the composition of the invention comprises DNA encoding a heterologous protein inserted between the subgenomic alphavirus promoter and DNA encoding the VSV G protein wherein the DNA encoding the heterologous protein is operably linked to DNA encoding a T2A peptide from Thosea asigna virus (Szymczak et al., 2004. Nature Biotechnology 22:589-594) which is in turn operably linked to DNA encoding the VSV G protein. In this way, expression of the heterogenous protein in the resulting VLVs of the invention is effectively tied to expression of the VSV G protein, the latter being essential for replication of the vector. Thus, expression of the heterologous protein is stabilized and the continued presence of the gene expressing this protein in the hybrid vector is assured.

In some embodiments, the 2A peptide is selected from the group consisting of equine rhinitis A virus (E2A), foot-and-mouth disease virus (F2A), porcine teschovirus-1 (P2A), Thosea asigna virus (T2A) and any 2A peptide or fragment thereof known in the art. In further embodiments, the 2A peptide is a T2A peptide or any T2A fragment thereof known in the art.

In certain embodiments, the heterologous gene can be under the control of an RNA virus promoter sequence that may not necessarily be an alphavirus subgenomic promoter sequence. Such modifications and variations of the RNA promoter sequence driving expression of the heterologous promoter sequences will become apparent to those skilled in the art as they practice the invention. The vector may also include conventional control elements which are operably linked to the heterologous gene in a manner which permits its transcription, translation and/or expression in a cell infected with the hybrid-virus vector produced by the invention.

As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. There are numerous expression control sequences, including promoters which are native, constitutive, inducible and/or tissue-specific, are known in the art that may be used in the compositions of the invention. "Operably linked" should be construed to include RNA expression and control sequences in addition to DNA expression and control sequences.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, individual elements may function either cooperatively or independently to activate transcription.

In one embodiment, a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The invention further includes the use of a tissue-specific promoter that drives expression of a given heterologous gene in one or more specific types of cells (e.g., desmin promoter, myoglobin promoter, muscle creatine kinase promoter, mammalian troponin 1 promoter, and skeletal alpha-action promoter). Furthermore, any artificial synthetic promoters known in the art can be used in this invention as these promoters can provide optimal efficiency and stability for the heterologous gene. Additionally, enhancer sequences regulates expression of the gene contained within a vector. Typically, enhancers are bound with protein factors to enhance the transcription of a gene. Enhancers may be located upstream or downstream of the gene it regulates. Enhancers may also be tissue-specific to enhance transcription in a specific cell or tissue type.

In order to assess the expression of the heterologous gene of interest, the expression vector to be introduced into a cell can also contain either a selectable marker gene or a reporter gene or both to facilitate identification and selection of expressing cells from the population of cells sought to be infected through the hybrid-virus vectors. In other aspects, the selectable marker may be carried on a separate piece of DNA and used in a co-infection/transfection procedure. Both selectable markers and reporter genes may be flanked with appropriate regulatory sequences to enable expression in the host cells. Useful selectable markers include, for example, antibiotic-resistance genes, such as the neomycin resistant gene and the like.

Reporter genes are used for identifying potentially infected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

It will be apparent to one skilled in the art that the invention is not limited to the nature of the heterologous gene that is expressed by the high titer hybrid-virus vector of the invention. Any suitable heterologous gene can be used where expression of the gene provides a benefit to the subject. For example, the heterologous gene may be a viral protein whose expression in a subject confers immunity to infection by the virus. Similarly, the heterologous gene may be a bacterial antigen, a parasitic antigen, a fungal antigen, a cancer antigen, an antigen involved in a deleterious autoimmune reaction, or any other protein where an immune response directed thereto provides benefit.

Heterologous Proteins

In the present invention, the high titer hybrid-virus vector of the invention may encode any heterologous protein useful in the invention, and may encode more than one heterologous protein inserted in tandem in the hybrid virus vector of the invention. Typically, the heterologous protein is a peptide fragment, polypeptide, protein or fusion protein. Optionally, the heterologous protein is suitable such that a cell mediated immune response is induced against it in a subject following administration of the vector to the subject.

In certain embodiments the heterologous protein is encoded by the a heterologous gene derived from a pathogenic organism which typically causes an infectious disease in a host. In certain embodiments, the pathogenic organism may be a prokaryotic cell, such as a gram positive or gram negative bacterium, or the pathogenic cell may be a protozoon, a parasite or a fungus, such as a yeast.

In certain embodiments, the pathogenic organism from which the heterologous protein is derived may be selected from the group consisting of, but not limited to: members of the genus *Escherichia, Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasteurella, Moraxella, Acinetobacter, Erysipelothrix, Branhamella, Actinobacillus, Streptobacillus, Listeria, Calymmatobacterium, Brucella, Bacillus, Clostridium, Treponema, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Coxiella, Borrelia* and *Mycoplasma*.

In certain embodiments, the heterologous protein may be a viral peptide. The virus from which the heterologous protein is derived may be selected from the group consisting of, but not limited to: human immunodeficiency virus (HIV), hepatitis A virus (HAV), hepatitis B (HBV), hepatitis C (HCV), any other hepatitis-associated virus, human papillomavirus (HPV) and especially high-risk oncogenic human papillomavirus types, Kaposi's Sarcoma-Associated Herpesvirus (KSHV) (also known as Human Herpesvirus-8 (HHV-8)), Herpes Simplex virus (HSV) (any subtype), Respiratory Syncytial Virus (RSV) and associated respiratory viruses, Influenza viruses, coronaviruses including SARS-associated Coronavirus (SARS-CoV), rhinovirus, adenovirus, SIV, rotavirus, human papilloma virus, arbovirus, measles virus, polio virus, rubella virus, mumps virus, papova virus, cytomegalovirus, varicella-zoster virus, varicella virus, huntavirus and any emergent virus, in particular Ebola virus, Marburg virus, West Nile virus (WNV), St Louis Encephalitis virus (SLEV), Rift Valley Fever virus (RVFV) and other members of the Bunyaviridae.

In some embodiments, the heterologous protein can be derived from a protozoan pathogen, the protozoa may typically be an intracellular protozoan, such as the apicomplexans *Plasmodium* spp., *Toxoplasma gondii* and *Cryptosporidium parvum*; or the trypanosomatids: *Leishmania* spp. and *Trypanosoma cruzi*.

In certain embodiments the heterologous protein can be derived from a yeast or fungi. The fungi may be derived from a genus selected from the group comprising: *Acremonium, Alternaria, Amylomyces, Arthoderma, Aspergillus, Aureobasidium, Blastochizomyces, Botrytis, Candida, Cladosporium, Crytococcus, Dictyostelium, Emmonsia, Fusarium, Geomyces, Geotrichum, Microsporum, Neurospora, Paecilomyces, Penicillium, Pilaira, Pityrosporum, Pneumocystis, Rhizopus, Rhodotorula, Saccharomyces, Stachybotrys, Trichophyton, Trichoporon,* or *Yarrowia*.

In some embodiments, the heterologous protein may be derived from a cancer. In such embodiments, heterologous protein is, or is a fragment of, a tumor specific antigen. In certain embodiments the cancer may be derived from the group including Acute and Chronic Myelogenous Leukemia (AML, CML), Follicular Non-Hodgkins lymphoma, malignant melanoma, Hairy Cell leukaemia, multiple myeloma, carcinoid tumors with carcinoid syndrome and liver and lymph node metastases, AIDS related Kaposi's sarcoma, renal cell carcinoma, adenocarcinoma of the large bowel, squamous cell carcinoma of the head and neck. The cancer may also be derived from organs and solid tissues, e.g., colon cancer, lung cancer, breast cancer, stomach cancer, prostate cancer, and endometrial cancer. When such heterologous proteins are used in the compositions and methods of the present invention, the resulting immune response generated may combat cancers and thus the vectors and viruses produced by these vectors are designed to be oncolytic.

In yet other embodiments, the heterologous protein may be associated with the pathology of an autoimmune disease. Organs and tissues commonly affected by autoimmune disorders include, but are not limited to, blood vessels, connective tissues, endocrine glands such as the thyroid or pancreas, joints, muscles, red blood cells and skin. Examples of autoimmune (or autoimmune-related) disorders for which such heterologous proteins may be useful include, but are not limited to, Addison's disease, Celiac disease, Dermatomyositis, Graves disease, Hashimoto's thyroiditis, Multiple sclerosis, Myasthenia gravis, Pernicious anemia, Reactive arthritis, Rheumatoid arthritis, Sjogren syndrome, Systemic lupus erythematosus and Type I diabetes.

Methods of the Invention

The vectors of the invention are useful in a variety of applications for generating VLVs useful for immunizing a subject against disease, and/or treating, preventing or diminishing risk of disease in a subject.

The invention therefore includes a method of immunizing a subject against a heterologous protein. The method comprises administering to the subject a composition comprising virus like vesicles (VLVs) produced by the high titer hybrid virus vector, wherein the high titer hybrid virus vector comprises DNA encoding a heterogeneous gene. Expression of the heterogeneous gene induces an immune response to the heterologous protein encoded thereby in the subject. The invention further includes a method of treating a subject in need thereof where the method comprises administering to the subject a composition comprising virus like vesicles (VLVs) produced by the high titer hybrid virus vector of the invention, wherein the high titer hybrid virus vector comprises DNA encoding a heterogeneous gene and wherein expression of the heterogeneous gene provides benefit to the subject. In one aspect, the invention includes a method of generating a memory T cell immune response to a heterologous protein in a subject. In another aspect, generating an adaptive B cell immune response to a heterologous protein in a subject.

Additionally included in the invention is a method of diminishing the risk that a subject will develop a disease. The method comprises administering to the subject a composition comprising the virus like vesicles (VLVs) produced by the high titer hybrid virus vector, wherein the high titer hybrid virus vector comprises DNA encoding a heterogeneous gene. Expression of the heterogeneous gene induces an immune response to the heterologous protein encoded thereby in the subject, thereby diminishing the risk that the subject will develop a disease associated with the heterologous protein.

The invention includes also a method of selecting high titer RNA virus like vesicles (VLVs). This selection is achieved by passaging in a cell culture a hybrid-virus vector comprising an RNA sequence encoding a viral structural protein, wherein the viral structural protein does not comprise an alphavirus structural protein and by screening the generated VLVs for high titer VLVs using extensive passaging of VLVs in cell culture, direct mutagenesis of the VLVs or any other selection method known in the art. In one aspect the hybrid-virus vector RNA sequence encodes an alphavirus non-structural protein. In another aspect the non-structural protein is a Semliki Forest virus (SFV) non-structural protein.

Pharmaceutical Compositions and Formulations.

The VLVs of the invention may be formulated as a pharmaceutical composition.

Such a pharmaceutical composition may be in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In one embodiment, the pharmaceutical compositions useful for practicing the method of the invention may be administered to deliver a dose of between $10^5$ and $10^9$ PFU.

In one embodiment, the pharmaceutical compositions useful for practicing the method of the invention may comprise an adjuvant. Suitable adjuvants contemplated by this invention include but are not limited to Freund's complete adjuvant, Freund's incomplete adjuvant, Quil A, Detox, ISCOMs or squalene.

Pharmaceutical compositions that are useful in the methods of the invention may be suitably developed for inhalation, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

The composition of the invention may comprise a preservative from about 0.005% to 2.0% by total weight of the composition. The preservative is used to prevent spoilage in the case of exposure to contaminants in the environment.

Administration/Dosing

The regimen of administration may affect what constitutes an effective amount. For example, the high titer hybrid-virus vector of the invention may be administered to the subject in a single dose, in several divided dosages, as well as staggered dosages may be administered daily or sequentially, or the dose may be continuously infused, or may be a bolus injection. Further, the dosages may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat the disease in the subject. An effective amount of the composition necessary to achieve the intended result will vary and will depend on factors such as the disease to be treated or prevented, the age, sex, weight, condition, general health and prior medical history of the subject being treated, and like factors well-known in the medical arts. In particular embodiments, it is especially advantageous to formulate the composition in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the composition and the heterologous protein to be expressed, and the particular therapeutic effect to be achieved.

Routes of Administration

One skilled in the art will recognize that although more than one route can be used for administration, a particular route can provide a more immediate and more effective reaction than another route. Routes of administration of any of the compositions\ of the invention include inhalation, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Kits

In some embodiments a kit is provided for treating, preventing, or ameliorating an a given disease, disorder or condition, or a symptom thereof, as described herein wherein the kit comprises: a) a compound or compositions as described herein; and optionally b) an additional agent or therapy as described herein. The kit can further include instructions or a label for using the kit to treat, prevent, or ameliorate the disease, disorder or condition. In yet other embodiments, the invention extends to kits assays for a given disease, disorder or condition, or a symptom thereof, as described herein. Such kits may, for example, contain the reagents from PCR or other nucleic acid hybridization technology (microarrays) or reagents for immunologically based detection techniques (e.g., ELISpot, ELISA).

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure. The materials and methods employed in the experiments disclosed herein are now described.

Materials and Methods

Reconstruction of the p50 VLV Genome into a Plasmid DNA.

The SuperScript III RT-PCR kit from Life Technologies and 15 DNA primer pairs were used with RNA from p50VLVs to generate overlapping dsDNA fragments covering the p50 VLV genome. Sequences of the fragments were determined (Yale Keck Facility) and assembled using DNAstar software. The plasmid pCMV-SFVG-CAP (FIGS. 1A-1B) was generated by replacing the SIV gag gene from plasmid pBK-SFVG-E660Gag with a synthetic gene encoding the SFV capsid protein. The 1,672-nucleotide deletion found in the p50 VLV genome sequence was introduced in pCMV-SFVGCAP (FIG. 5) using a synthetic DNA fragment spanning the Bpu10I-SpeI sites. The remaining mutations were introduced step-wise using the indicated restriction fragments prepared by RT-PCR from p50 VLV RNA. Specific point mutations were generated using the Quik-Change II mutagenesis kit from Agilent Technologies.

Titering of VLVs.

The p50 VLVs were routinely titered using serial dilutions and a standard 2-d plaque assay on BHK-21 (ATCC CCL 10) cell monolayers. Low titer VLVs plaques were counted using a dissecting microscope or were titered using indirect immunofluorescence microscopy to detect VSV G protein expression in infectious centers.

Purification of p50 VLVs.

Approximately 107 BHK-21 cells in DMEM with 5% (wt/vol) FBS were infected with p50 VLVs at an MOI of 10 and incubated for 24 h at 37°. The medium was then centrifuged at 800×g for 5 min to remove cells and cell debris. 10 ml of medium was then layered onto 28 mL of 10% (wt/vol) sucrose in PBS and centrifuged at 25,000 rpm for 1.25 h in a Beckman SW28 rotor. The pellet of VLVs was resuspended in 200 μL of PBS and then layered onto 4.5 mL of 10% sucrose in PBS and centrifuged at 40,000 rpm for 1 h in a Beckman SW41 rotor. The pellet was resuspended in 100 μL of PBS. VSV virions were grown and purified in parallel to provide markers for SDS/PAGE gel electrophoresis.

Electron Microscopy of VLVs and VLV-Infected Cells.

VLVs prepared as above (~5 μL) were applied to carbon-coated EM grids made hydrophobic by plasma ionization. Grids were fixed in 1% glutaraldehyde for 2 min, followed by washing in PBS (pH 7.4) and water, then stained with 2% (wt/vol) uranyl acetate and air-dried. For immunogold labeling, the samples were applied to grids that had been preincubated with PBS containing 1% BSA. Unfixed samples on girds were incubated directly with a mouse monoclonal antibody to VSV G, washed with PBS containing 1% BSA and incubated with donkey anti-mouse IgG conjugated to 12 nm gold particles (Abcam). Grids were then washed and stained with 2% (wt/vol) phosphotungstic acid and then dried. Grids were viewed in a FEI 120 kV transmission electron microscope. The digital images were acquired with a Gatan 4 k×4 k CCD camera.

BHK cells infected with VLVs were fixed at room temperature for 1 h in 0.1 M sodium cacodylate buffer (pH 7.4) containing 2% (wt/vol) glutaraldehyde. After rinsing with the same buffer, cells were postfixed in 0.5% OsO4 at room temperature for 30 min. Specimens were then stained en bloc with 2% aqueous uranyl acetate for 30 min, dehydrated in a graded series of ethanol to 100%, and embedded in Poly/bed 812 for 24 h. Thin sections (60 nm) were cut with a Leica ultramicrotome and poststained with uranyl acetate and lead citrate. Sample grids were examined in a FEI Tencai Biotwin transmission electron microscope at 80 kV. Images were taken using a Morada CCD camera fitted with iTEM (Olympus) software.

The results of the experiments are now described in the following examples.

Example 1: Extensive Passaging Generates High-Titer VLVs

Figure 1B:
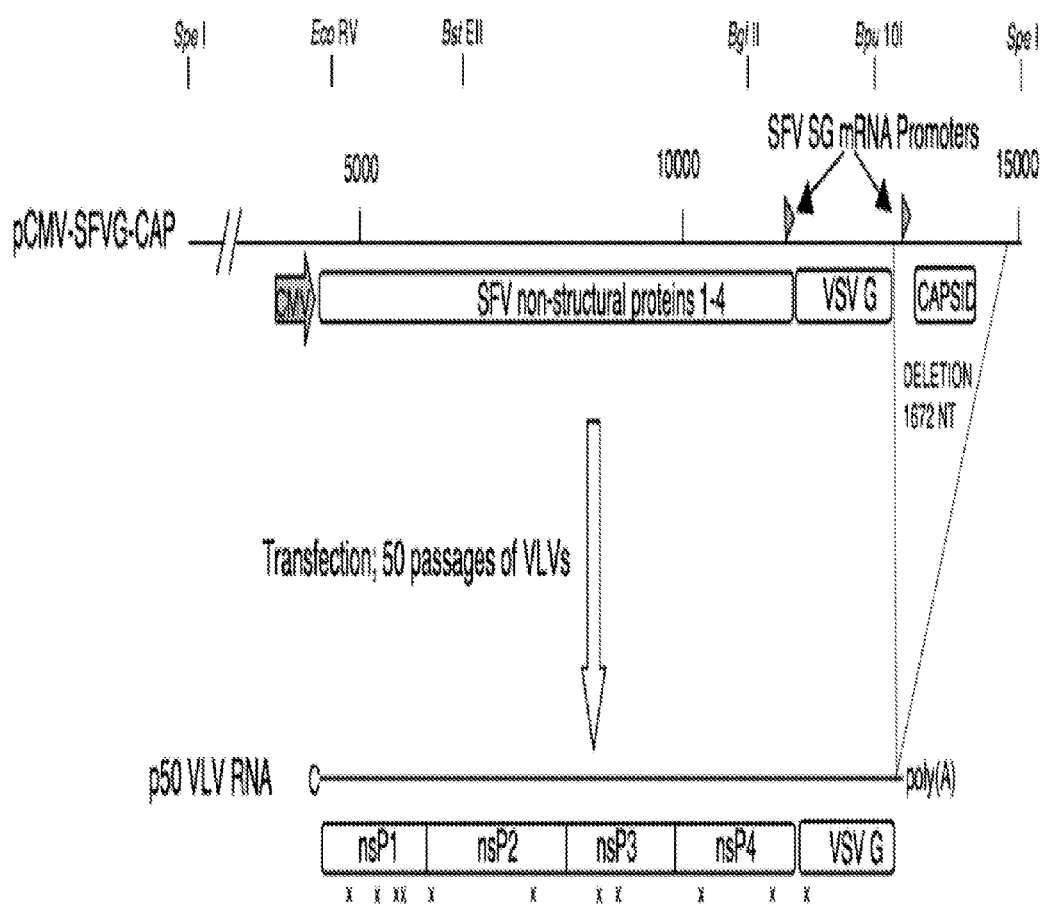
Figure 2:
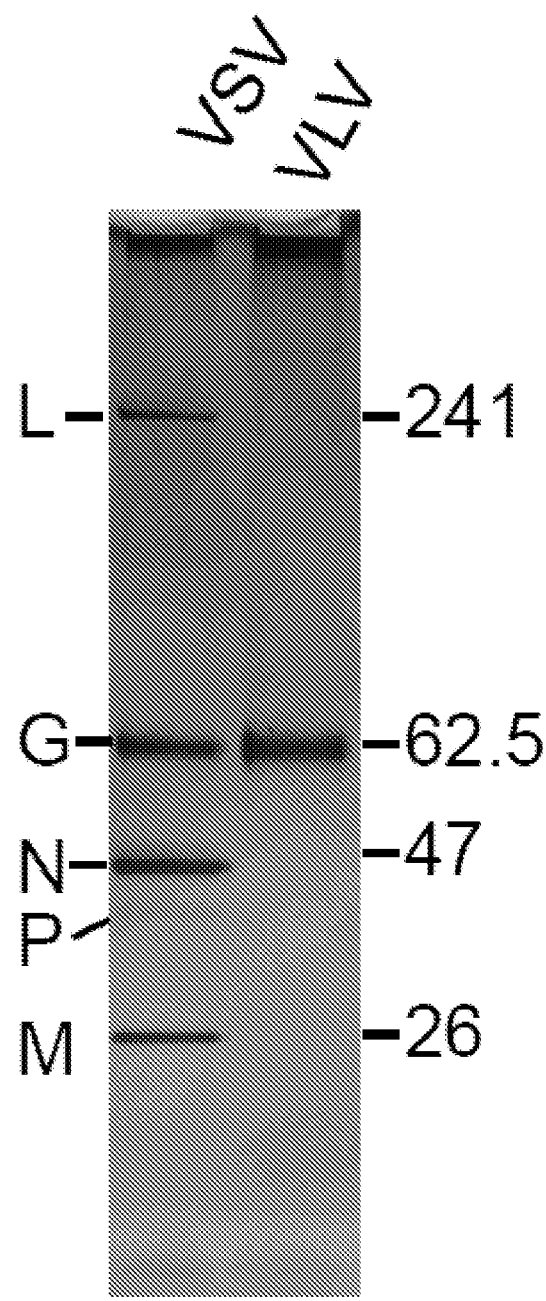
Figures 3A, 3B, 3C, 3D:
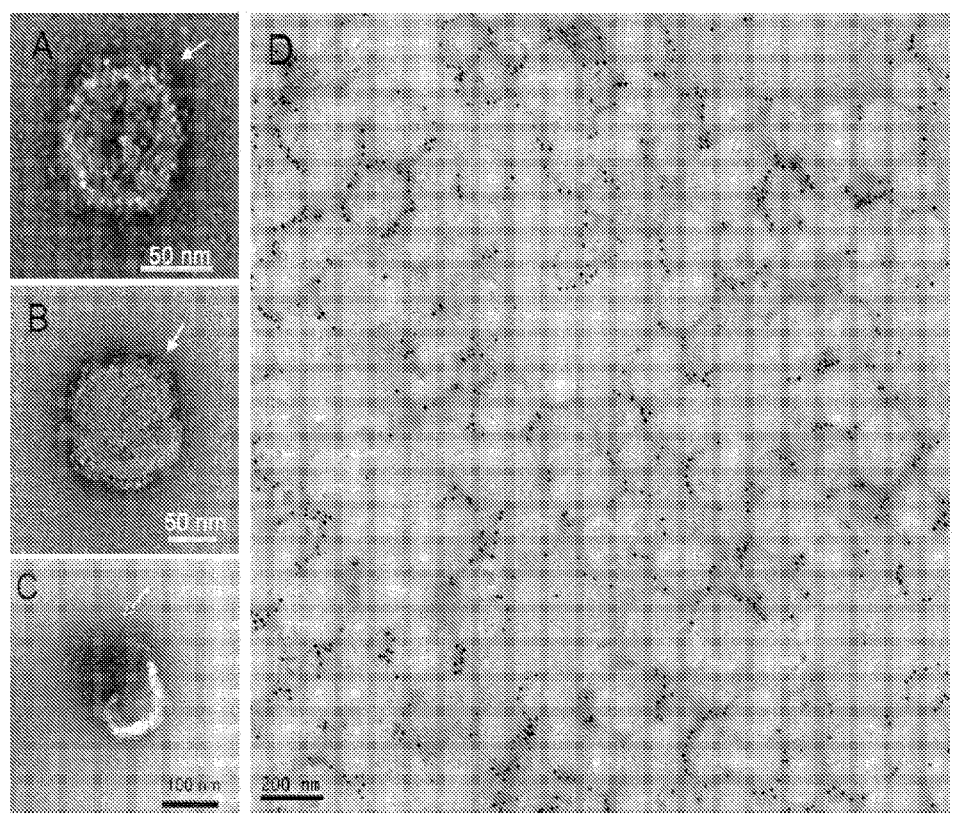
Figures 4A, 4B:
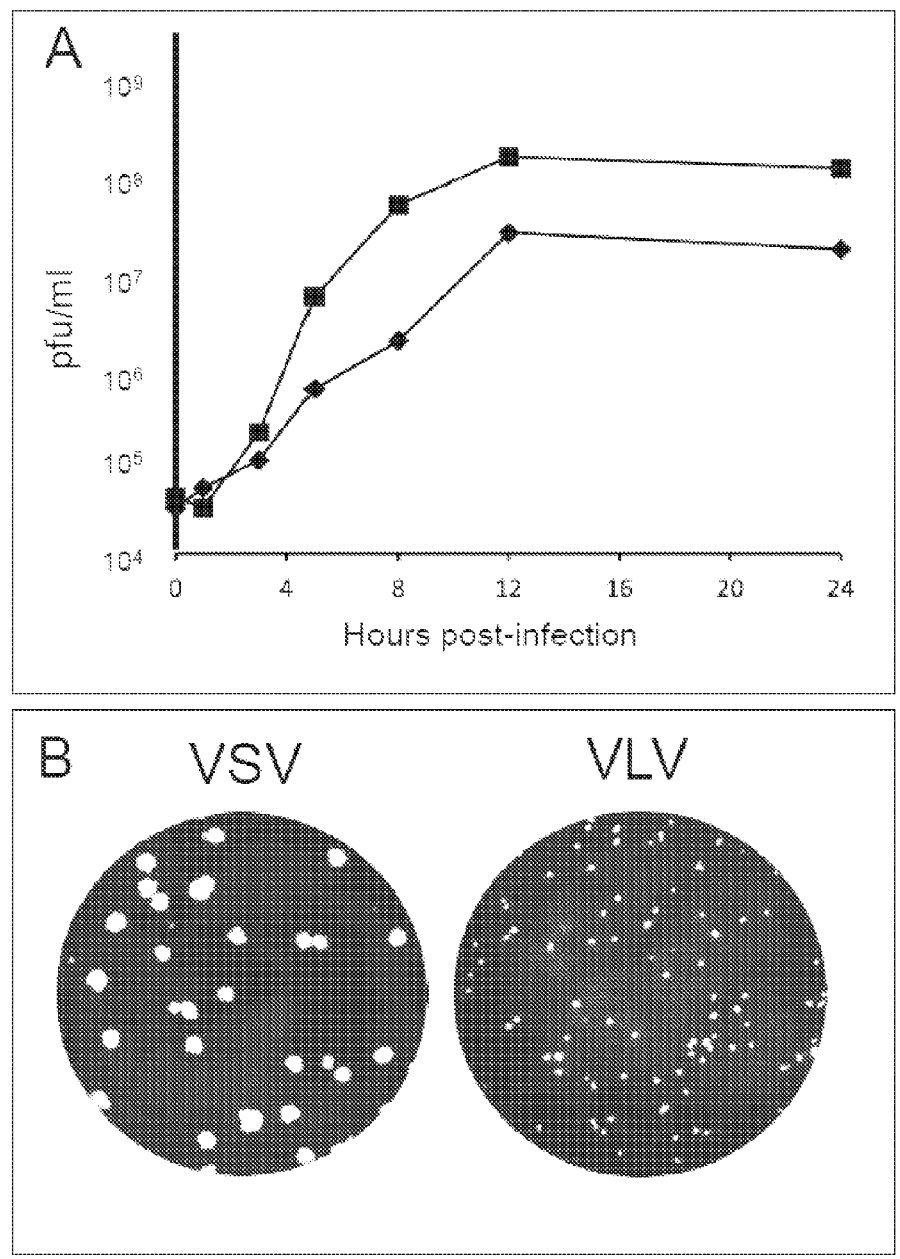

To generate VLVs that grow to high titers following evolution though extensive passaging in tissue culture, the starting DNA construct diagramed in FIGS. 1A-1B was used. The SFV replicon RNA generated using this construct expresses VSV G from the first subgenomic promoter and the SFV capsid protein from the second promoter. Infectious particles from this construct were derived and found to exhibit low titers typical of VLVs (~$10^5$ infectious units/ml). Passaging of the VLVs on BHK cells was pursued over a period of one year to determine if it was possible to evolve particles that would grow to higher titers. In the initial passages 5% of the medium from cells showing cytopathic effect (CPE) were transferred onto fresh BHK cells on 6 cm dishes, and strong CPE then developed by 3-5 days. Expression of the SFV capsid protein was completely lost by passage eight suggesting that its expression was inhibiting particle production. With continued passaging an increasing particle titers and a much more rapid CPE developing in less than 24 hours were noticed. By passage fifty the VLVs had evolved to reach titers >5×$10^7$ pfu/ml and they formed visible plaques of variable sizes on BHK cells after two days. At this point a large plaque was chosen and used to generate a cloned VLV stock which will be referred to subsequently as "p50 VLV". This p50 VLV grows to titers of approximately $10^8$ pfu/ml, an increase of approximately 1000-fold over the starting vector.

The growth rate of the VLVs to VSV were compared using traditional one-step growth curves. It was found that the maximal VLV titers (~$10^8$ pfu/mL) were typically reached by between 12 and 24 h after high multiplicity infection. In contrast, maximal VSV titers (~$10^9$ pfu/mL) were reached between 10 and 12 h after infection.

Example 2: Purified p50 VLVs Contain VSV G as the Only Structural Protein

To determine what proteins were in the p50 VLVs, BHK cells were infected with p50 VLVs or with VSV at a multiplicity of infection (MOI) of ~10) on 10 cm dishes. After 24 h when the cells showed extensive CPE, the VSV particles or the VLVs in the medium were purified through two rounds of ultracentrifugation. The proteins in the VLVs and VSV particles were then analyzed by SDS-PAGE followed by silver staining. As shown in FIG. 2, VSV virion particles contained the five proteins N, P, M, G and L, while the purified p50 VLV particles contained VSV G protein as the only apparent structural protein. There was no trace of the SFV capsid protein (29.8 kDa) consistent with the loss of its expression during early passages. The total yield of VLV protein from 5×$10^6$ BHK cells infected with the p50 VLVs was approximately 20 μg, while the same number of cells infected with VSV yielded about 60 μg of total viral protein. No measurable protein yields were recovered from medium derived from uninfected BHK cells.

Example 3: Characterization of the p50 Particles by Electron Microscopy

The purified particles used for the protein characterization were imaged by transmission electron microscopy (TEM) following glutaraldehyde fixation and negative staining with uranyl acetate. Examples are shown in FIGS. 3A-3C. Many of the particles appeared to have protein spikes, presumably VSV G protein (VSVG), on their surfaces (arrows). Some of the particles prepared for TEM by this method also appeared to be broken and were releasing nucleic acid (FIG. 3C).

Next, TEM was performed on VLV particles that were unfixed, and labeled with antibody to VSV G followed by a secondary antibody conjugated to 12 nm gold particles. The particles were then negative-stained with phosphotungstic acid (FIG. 3D). The TEM image shows clear surface labeling of numerous vesicles with a halo of gold particles indicating the presence of VSV G on their surfaces. Vesicle diameters were in the 50-200 nm range. The size distribution was similar to what was observed for the low titer VLVs described previously (U.S. patent Ser. No. 12/747,59; Rolls et al., 1994. Cell 79:497-506 and Rolls et al., 1996. Virology 218:406-41).

Example 4: Growth of the p50 VLV Particles

To examine the growth rate of the p50 VLVs in comparison to VSV, a traditional one-step growth curve (FIG. 4A) was performed. Cells were infected at an multiplicity of infection (MOI) of 10 with either p50 VLVs or VSV, input particles were then removed, and then samples were taken from the medium at the indicated times and titered by plaque assay. The growth rate of the VLVs was similar to VSV with the maximal titer reached by twelve hours after infection. The VLV titers were about 8-10 fold lower than VSV, consistent with the smaller plaque size (FIG. 4B).

Example 5: Sequence of the p50 VLV Genome

To determine a consensus sequence of the p50 VLV genome reverse transcription and PCR were performed to generate overlapping DNA fragments covering the entire genome, and then these fragments were sequenced. The assembled sequence revealed a large deletion of 1672 nucleotides (in vector deletion located between nucleotides 13333 and 13334) which had removed the second SFV promoter, the entire capsid gene, and all except 187 nucleotides of SFV sequences preceding the poly(A) (FIG. 1).

In addition to this deletion, there were 16 single base changes listed in Table 1 below. Ten of these changed amino acids in all four of the SFV non-structural proteins, one changed an amino acid in VSV G, and four mutations were silent (FIG. 1, Table 1).

TABLE 1

Nucleotide and amino acid changes in p50VLVs.

| Nucleotide change | Amino acid change and context* | Protein affected |
|---|---|---|
| G-4700-A | G-106-E (AAS<u>E</u>KVL) | nsP1 |
| A-5424-G | None | |
| G-5434A | V-351-I (ATD<u>I</u>TPE) | nsP1 |
| T-5825-C | L-481-S (KRE<u>S</u>IPV) | nsP1 |
| T-5930-C | I-516-T (LVP<u>T</u>APA) | nsP1 |
| A-6047-G | D-555-G (QPN<u>G</u>VLL) | nsP2 |
| G-6783-A | None | |
| G-6963-A | None | |
| G-7834-A | A-1151-T (ALV<u>T</u>EYK) | nsP2 |
| T-8859-A | None | |
| T-8864-C | M-1494-T (AID<u>T</u>RTA) | nsP3 |
| G-9211-A | A-1610-T (ERI<u>T</u>RLR) | nsP3 |
| A-10427-G | N-2015-S (TLQ<u>S</u>VLA) | nsP4 |
| G-11560-A | E-2393-K (SRY<u>K</u>VEG) | nsP4 |
| A-11871-G | N-34-D (NWH<u>D</u>DLI) | VSV G |
| T-11978-C | None | |

*Amino acids are numbered in the SFV nsP1-4 polyprotein, or in the VSV G protein. Bold underlined text indicates the amino acid that was changed.

The nucleotide sequence of the high titer hybrid-virus vector: pCMV-SFVG-p50R (referred as SEQ ID NO: 1) is provided elsewhere herein at the end of the "Examples" section.

Example 6: Reconstruction of p50 VLV Replicon in a DNA-Launched Vector

Figure 5:
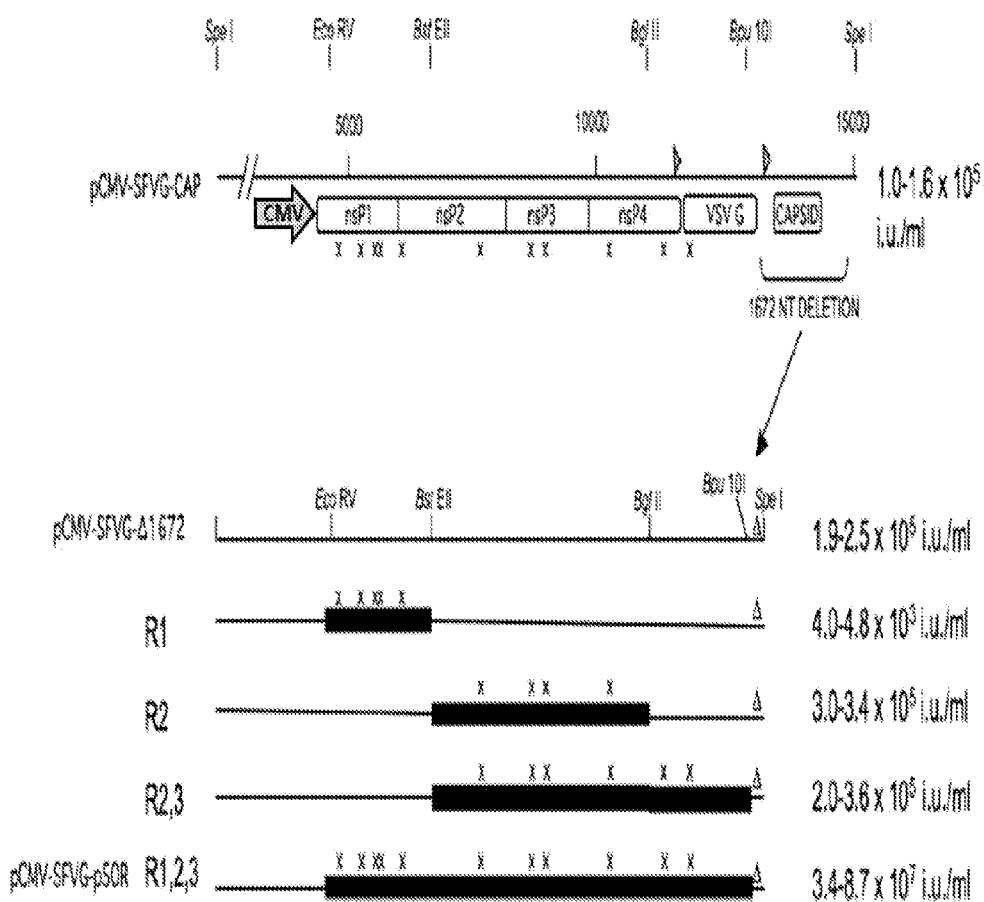

To reconstitute high-titer p50 VLV sequence into a plasmid DNA and to determine what sequence changes were responsible for generating the high-titer phenotype in the p50 VLVs, a stepwise reconstruction of the p50 VLV sequence was initiated in the DNA launched vector (FIG. 5). First the "1672" nucleotide deletion was introduced into a plasmid using a synthetic DNA fragment containing the deletion. This fragment was inserted between the unique Bpu10I and Spe I sites of pCMV-SFV-GCAP to generate pCMV-SFVG-Δ1672. This construct did not produce the high-titer VLVs (only 2×10$^5$ per ml) indicating that the deletion had only a small effect on increasing VLV titers. Then a reverse transcription and PCR of p50 VLV RNA were used to generate DNA fragments spanning the indicated restriction sites, EcoRV-BstEII, BstEII-BglIII, and BglIII-Bpu10I. These fragments containing the p50 VLV mutations were then used to replace the corresponding fragments in the pCMV-SFVG-Δ1672 plasmid DNA to generate the recombinants labeled R1, R2, R2,3 and R1,2,3. All constructs were sequenced, and any that did not match the p50 VLV consensus were discarded. Interestingly, after transfection of these initial recombinants onto cells, they yielded variable titers, but none generated high-titer p50, plaque-forming VLVs. However, when all of the mutations were put together in recombinant R1,2,3, (plasmid designated pCMV-SFV-G-p50R) the high-titer phenotype was recovered. These results suggested that some combination of evolved mutations was required to generate the high-titer phenotype. They also indicated that incorporation of subsets of the mutations (for example in the R1 recombinant) were deleterious to replication. It was also determined in later constructs that the mutation N34D in the VSV G ectodomain was not required for generation of the high titer VLVs.

To determine whether the enhancing mutations were affecting replicon RNA synthesis, Northern blots were performed to detect replicon RNA or subgenomic G mRNA in cells infected with VLVs derived from pCMV-SFVG-Δ1672 or pCMV-SFVG-p50R. We saw no significant differences in the amounts of RNA or in the ratio of replicon to subgenomic RNA in the cells (FIG. 10).

Figures 6A, 6B, 6C, 6D, 6E:
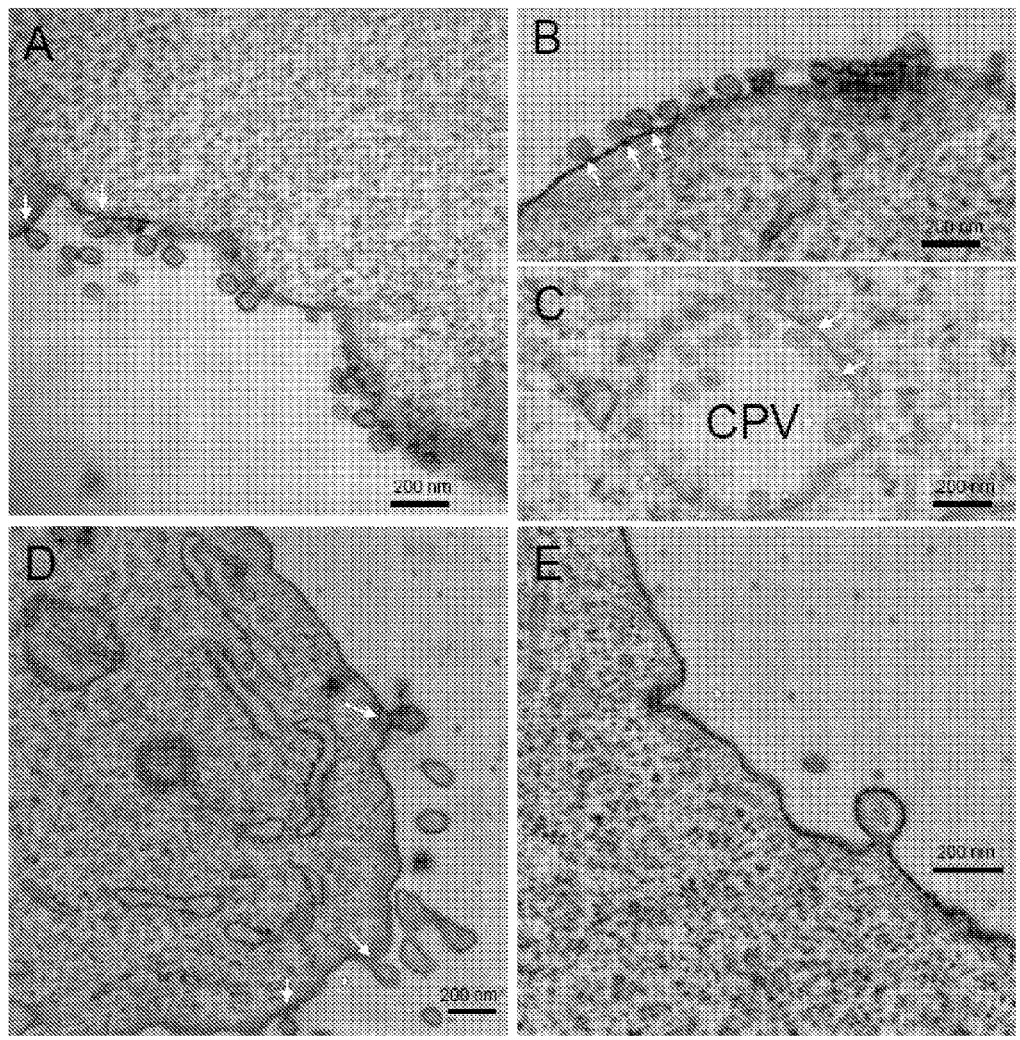

Example 7: TEM of Infected Cells Suggests a Possible Mechanism for Generation of the High-Titer VLVs In prior studies of the VLVs generated by expression of VSV G protein from the SFV replicon, the mechanism that generated even low titer infectious vesicles was not determined (U.S. application Ser. No. 12/747,59; Rolls et al., 1994. Cell 79:497-506 and Rolls et al., 1996. Virology 218:406-411). A possible explanation was that they were derived from SFV replication complexes that had been seen largely in membrane invaginations called spherules within cytopathic vacuoles (CPVs), but also occasionally on the cell surface (Froshauer et al., 1988. The Journal of Cell Biology 107:2075-2086; Grimley et al., 1968. Journal of Virology 2:1326-1338). More recent studies have shown that SFV spherules initially form at the cell surface, and are then endocytosed, eventually accumulating in the cytoplasmic CPVs (Spuul et al., 2010. Journal of Virology 84:7543-7557). To examine budding of the low versus the high-titer VLVs, VLVs from the construct containing the 3' deletion (pCMV-SFVG-Δ1672) and from the R1, 2, 3 construct (pCMV-SFVG-p50) containing the deletion and the 16 point mutations were first prepared. These were used to infect cells and TEM of fixed, thin sections of cells at seven hours after infection was conducted. The plasma membranes of cells infected with the low titer (Δ1672) VLVs showed numerous ~60-70 nm spherical structures that often appeared to be attached to the cell surface by a thin "neck" (FIGS. 6A and 6B, arrows). Intracellular vacuoles that are the typical CPVs containing SFV spherules attached by a neck to the membrane (FIG. 6C) were also found. These spherules on the cell surface appeared virtually identical to the spherical structures seen in the CPVs, often including a dense central spot that is thought to be RNA (Froshauer et al., 1988. The Journal of cell biology 107:2075-2086).

In contrast to the results with the low titer VLVs, cells infected with the p50 VLVs showed only occasional vesicles that appeared to be budding from the cell surface (FIGS. 6 D and 6E). These also appeared in many cases to be connected by a neck-like structure (arrows). These results suggested that the p50 VLVs might be budding efficiently, whereas the low titer VLVs remained attached at the cell surface.

Example 8: A Late Domain Motif was Selected in the p50 VLV nsP1 Protein

Many enveloped viruses that bud from the cell surface recruit a cellular budding machinery (called an ESCRT complex) that cells normally use to sort cargo into vesicles that bud into multivesicular bodies (Votteler and Sundquis, 2013. Cell host & microbe 14:232-241; Weiss, E. R., and H. Gottlinger, 2011. Journal of molecular biology 410:525-533). These viruses have sequence motifs called late domains in their internal membrane proteins that recruit components of the ESCRT complex to the budding site. Mutations in these motifs result in incomplete budding of virus particles from the cell and retention by a membranous neck. Because the low titer VLVs appeared to retain large numbers of spherules on the cell surface, the sequence changes in the p50 VLV genome were examined to determine whether the passaging might have selected for a late domain sequence in any of the SFV nonstructural proteins. In fact one of the four mutations in nsP1 was found to have changed the amino acid sequence PIAP to PTAP near the C-terminus of nsP1 (Table 1). P(T/S)AP is a common motif in internal viral membrane proteins that binds to the protein tsG101 to initiate recruitment of the an ESCRT protein complex and facilitate virus budding; nsP1 is the membrane anchor of the SFV replication complex consisting of a complex of nsP1, 2, 3 and 4.

Example 9: Additional Evidence that the High-Titer p50 VLVs are Using the ESCRT Pathway in Budding Ubiquitination is often involved sorting of cargo into multivesicular bodies (MVB), and inhibitors of ubiquitination such as MG-132 often inhibit budding of viruses (e.g. HIV) that hijack the MVB/ESCRT pathway (Taylor et al., 2007, Journal of Virology 81:13631-13639; Weiss and Gottlinger, 2011, Journal of Molecular Biology 410:525-533). Using this concept, it was shown that MG-132 treatment of cells after infection with the p50 VLVs inhibited the production of the high-titer p50 VLVs by 55-fold. This inhibition was consistent with the idea of p50 VLVs use the ESCRT pathway to promote budding. The experiment was performed as follows: BHK cells were infected with the p50 VLVs (10 pfu/cell) for one hour, washed and then incubated in the presence or absence of 100 uM MG-132 for 24 h. VLV titers were then determined by plaque assay.

Example 10: The PTAP Motif is Necessary but not Sufficient for High-Titer Particle Release The results obtained with the R1 recombinant, shown in FIG. 5, suggest that the PTAP motif is not sufficient to generate the high-titer VLVs. However, this interpretation is confounded by the presence of three other mutations in the nsP1 and one in nsP2 that might be deleterious in the absence of the other mutations. To determine if the PTAP mutation was required for high-titer particle production, only the PTAP motif in the fully reconstituted p50 vector (pCMVSFVG-p50R, FIG. 5) was mutated and changed back to the original PIAP sequence. The titers obtained for the PIAP and PTAP constructs following transfection onto BHK cells were then compared. The titers obtained at 48 hours after transfection were $1.2 \times 10^6$ i.u/ml for PIAP and $1 \times 10^8$ i.u./ml for PTAP indicating an important role for the PTAP motif in generating the high titer.

Figure 7:
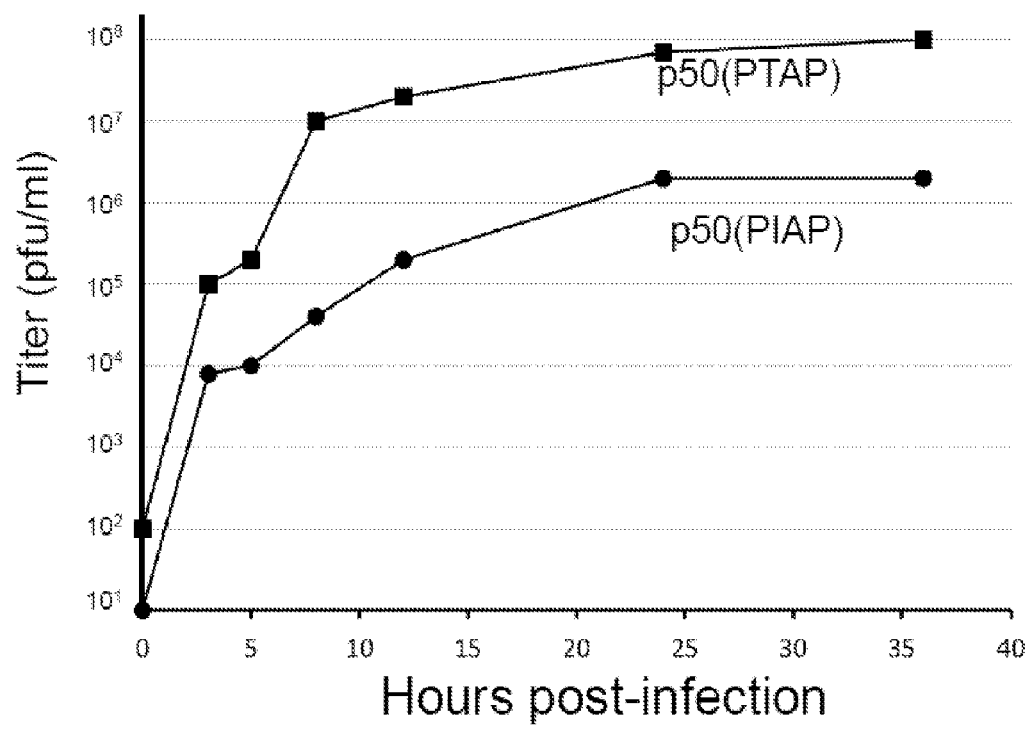

Additionally, a one-step growth curve using the infectious VLVs derived from these transfections was performed to analyze the kinetics of infectious p50VLV-PTAP, and p50VLV-PIAP release. The results of this experiment are shown in FIG. 7. Both constructs showed similar kinetics of growth reaching plateau by 24 h. However, p50-PIAP mutant yield was reduced 50 to 100-fold compared to p50-PTAP at the later time points. These results indicate that the PTAP motif is necessary for efficient generation of the VLVs.

To determine whether the PTAP mutation was sufficient for generating high titer VLVs, a mutation generating the PTAP motif alone was introduced into the pCMV-SFVG-Δ1672 plasmid (FIG. 5) and derived VLVs. The VLV titers obtained after transfection of this DNA onto cells were only $1.1 \times 10^5$ per mL, indicating that the PTAP motif alone was not sufficient to drive efficient VLV production.

Example 11: Stabilization of Foreign Gene Expression in High-Titer VLVs

In previous studies using VLVs as vaccine vectors the foreign genes from second subgenomic mRNA promoters were found to be expressed (Rose et al., 2008. PNAS 105:5839-5843; Schell et al., 2011. Journal of Virology 85:5764-5772). It was also found that the expression of the foreign genes was often lost after only 2-3 passages of VLVs (Rolls et al., 1996. Virology 218:406-411; Rolls et al., 1994. Cell 79:497-506). Loss typically involved a deletion that included the second promoter and some or all of the second gene. To determine if it is possible to generate greater genetic stability in the VLVs, a new strategy was developed based on linking in a single mRNA the expression of the essential G gene to the expression of the non-essential foreign gene. To obtain equimolar expression of the foreign protein and VSV G the two open reading frames (ORFs) were linked together separated by the 18 amino acid T2A peptide from Thosea asigna virus (Szymczak et al., 2004. Nature Biotechnology 22:589-594). This peptide and other related peptides have been used to express multiple proteins from single mRNAs (Szymczak-Workman et al., 2012. Cold Spring Harbor protocols 2012:199-204). Although these peptides were initially believed to be self-cleaving, it is now thought that they cause ribosomal "skipping". Ribosome function is modified by the peptide preventing peptide bond formation between the terminal Gly and Pro causing release of the upstream protein but allowing continued translation of the downstream peptide (Szymczak-Workman et al., 2012. Cold Spring Harbor protocols 2012:199-204). By placing the foreign gene upstream of VSV G, there should be a strong selection to maintain expression of the upstream reading frame.

Figure 8A:
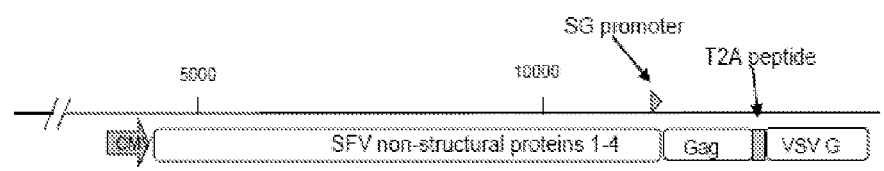
Figure 8B:
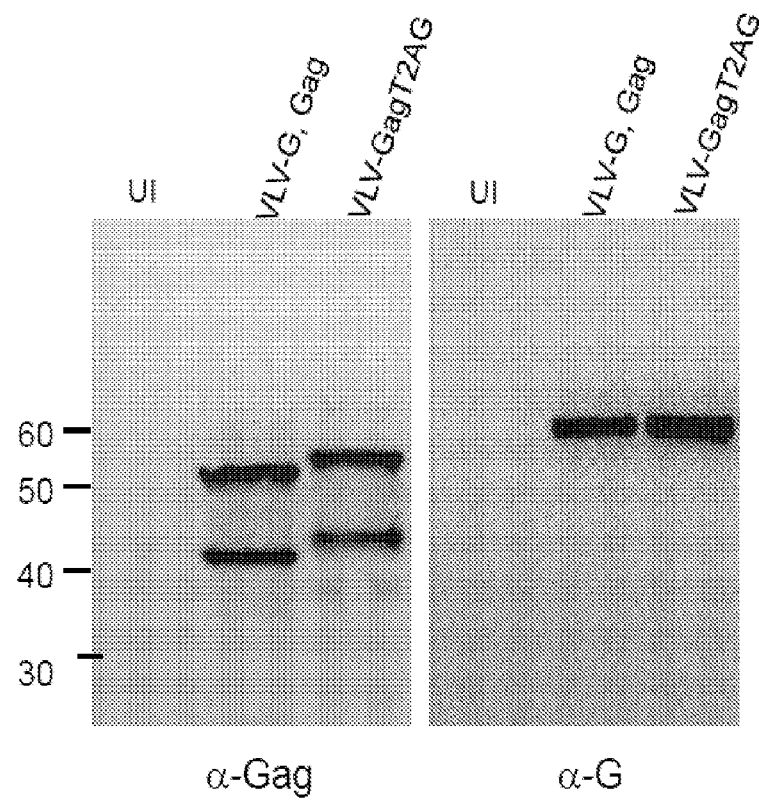

This strategy was tested by placing an simian immunodeficiency virus (SIV) gag gene ORF upstream of the VSV G gene ORF separated by the 18 amino acid T2A peptide (EGRGSLLTCGDVEENPGP, SEQ ID NO: 2) as diagrammed in FIG. 8A. This expression cassette was cloned into the pCMV-p50R vector in place of the single G gene behind the single subgenomic SFV promoter. VLVs recovered from this construct grew to titers of at least $10^8$ pfu/ml showing that expression of the extra gene did not reduce VLV titers significantly. Expression of both Gag and G from cells infected with the VLVs was verified by SDS-PAGE and western blotting with antibody to SIV Gag and VSV G (FIG. 8B). The C-terminal extension of the T2A peptide on Gag caused a decrease in the mobility of Gag and a Gag cleavage product when compared to Gag expressed from separate subgenomic promoters (FIG. 8B). VLVs expressing Gag from separate promoters showed loss of Gag expression after only five passages, while Gag expressed linked to G by the T2A peptide was stable for at least ten passages.

Example 12: Safety Studies with High-Titer VLVs

In the vaccination studies of this invention, using intranasal or intramuscular routes with low or high-titer VLVs, no weight loss or other signs of pathogenesis in mice were observed. The possible toxicity of the high-titer VLVs was also examined by infusing $5 \times 10^6$ PFU into the tail vein of mice. No weight loss, no behavioral modification, and no other signs of neurological dysfunction were observed in the mice. The potential of a neurovirulence related to the high titer VLVs was also tested by the intracranial (IC) route. Adult mice (n=5) were injected stereotactically with $10^5$ PFU of VLVs into the left frontal lobe of the brain using a Hamilton syringe. The mice were observed for six weeks and remained healthy with no signs of any neurological dysfunction or any other adverse signs. In contrast, even 10 PFU of VSV given by this route causes a lethal encephalitis within 10 days. Thus, despite the abundance of VSV G protein on the particles, they are not pathogenic in the brain, presumably because their replication in vivo is very limited. Unlike real enveloped RNA viruses these VLVs lack a nucleocaspid to protect their RNA and are likely controlled very rapidly by innate immune responses.

Example 13: The High-Titer VLV Particles Retain Immunogenicity

To determine if the high-titer VLVs retained immunogenicity, mice were vaccinated intra-muscularly with either $10^6$ or $10^5$ plaque forming units (PFU) and after 28 days the serum was tested for neutralizing antibody (nAb) to VSV. On average the VSV nAb titers were 1:960 ($10^6$ PFU group) and 1:640 ($10^5$ PFU) after this single vaccination. Unvaccinated mice had no detectable nAb (<1:20). These results indicate that the passaged VLVs retained the ability to generate potent nAb responses).

Example 14: Model for Generation of the Low and High-Titer VLVs

FIGS. 9A-9C show a model for generation of the high-titer VLV particles. FIG. 9A shows that SFV replicons not encoding VSV G are initially formed at the plasma membrane in the light-bulb shaped spherules. These spherules are then rapidly endocytosed and ultimately accumulate in the classic cytopathic vacuoles (CPVs) seen in cells containing SFV replicons (Spuul et al., 2010. Journal of Virology 84:7543-7557). In the case of SFV replicons expressing VSV G on the surface, the endocytosis of the spherules is likely inhibited by VSV G (Whitaker-Dowling et al., 1983. Virology 131:137-143; Wilcox et al., 1983. The Journal of Cell Biology 97:1444-145), resulting in high levels of spherules trapped on the cell surface as seen in FIGS. 9A and 9B. These spherules cannot bud efficiently, but are occasionally released from the cell surface to infect neighboring cells. After extensive passaging of VLVs, multiple mutations were selected including one mutation generating a "late domain" PTAP motif near the C-terminus of the SFV nsP1 protein. This mutation was selected for because it caused release of the VLVs from the cell surface. Additional mutations in the nsP proteins may contribute to higher particle production, perhaps by allowing greater exposure of the PTAP motif to the ESCRT complex and rapid scission of the spherules from the cell surface (FIG. 9C).

The requirement for more than one mutation to generate the high-titer VLV phenotype is consistent with the extensive passaging required to evolve the high-titer VLV. The model presented herein is based in part on the observation that large numbers of approximately 60- to 70-nm spherule-like structures are present on the surfaces of cells infected with low titer VLVs, whereas cells infected with VLVs containing the PTAP and other mutations showed only occasional vesicles apparently budding from the cell surface. A similar accumulation of HIV-1 and other viruses is seen when viruses have mutations in their late domain motifs (Weiss et al., 2011, J Mol Biol 410(4):525-533; Göttlinger et al., 1991, Proc Natl Acad Sci USA 88(8):3195-3199). If the VLVs were derived exclusively from the budding of spherules, one might expect the purified p50 VLVs to have a more uniform diameter. However, the purified VLVs observed herein and previously by TEM (Rolls et al., 1994, Cell 79(3):497-506) ranged in diameter from about 50-200 nm. One possible explanation for the range of sizes is fusion of two or more VLVs, potentially catalyzed by VSV G, to generate larger vesicles. It is also possible that only the smaller VLVs are derived from spherules, and that the larger vesicles are generated through some other mechanism.

All positive-strand RNA viruses use some type of membrane bound compartments to sequester their RNA during replication. For some viruses there is evidence that these compartments are lined with a shell of replicase proteins. In the case of SFV, there is no evidence that the spherules contain a replicase protein shell. The nsPs appear to be located on the cytoplasmic side of the spherule neck (Froshauer et al., 1988, J Cell Biol 107(6 Pt 1):2075-2086). The membrane invaginations formed in the generation of multivesicular bodies by the ESCRT pathway lack an internal protein shell and resemble the SFV spherules. Thus, it is possible that some components of the ESCRT pathway are normally involved with SFV spherule formation, but the components required for membrane scission are lacking or inhibited. The mutations selected in the p50 VLVs could result in recruitment of additional components required for scission or might release the inhibition of scission. Silver staining (FIG. 2 and FIGS. 3A-3D) revealed that structural proteins were not detected expect for VSV G in the p50 VLVs, suggesting that there is no major component forming a protein shell within them.

While not being bound by theory, it is interesting to speculate that at some early stage in the evolution of enveloped RNA viruses, spherules may have been the direct precursors of primitive virus particles that budded from cells and lacked capsids. Capsids may have evolved later to allow more efficient packaging of RNA, greater virus stability, and shielding from recognition by innate immune mechanisms.

In parallel studies related to the present invention, examining the immunogenicity and potential pathogenicity of the p50 VLVs showed that the VLVs of this invention retain immunogenicity and lack pathogenicity. Thus, these evolved VLVs have significant potential as vaccine vectors and for various vaccine applications or for priming and boosting.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

```
Nucleotide sequence (5'-3') of the high titer hybrid-virus vector: pCMV-SFVG-p50R
                                                                    (SEQ ID NO: 1)
5'-CTAGTGCATCCAAAGAATTCAAAAAGCTTCTCGAGAGTACTTCTAGAGCGGCCGCGCATCGATTTTCCACCCGGGTGGGGTACCA GGTAAGTGTACCCAATTCGCCCTATAGTGAGTCGTATTACAATTCACTGGCCGTCGTTTTACAACGTCGTGACTGGGAAAACCCTGGC
```

-continued

```
GTTACCCAACTTAATCGCCTTGCAGCACATCCCCCTTTCGCCAGCTGGCGTAATAGCGAAGAGGCCCGCACCGATCGCCCTTCCCAAC

AGTTGCGCAGCCTGAATGGCGAATGGAGATCCAATTTTTAAGTGTATAATGTGTTAAACTACTGATTCTAATTGTTTGTGTATTTTAG

ATTCACAGTCCCAAGGCTCATTTCAGGCCCCTCAGTCCTCACAGTCTGTTCATGATCATAATCAGCCATACCACATTTGTAGAGGTTT

TACTTGCTTTAAAAAACCTCCCACACCTCCCCCTGAACCTGAAACATAAAATGAATGCAATTGTTGTTGTTAACTTGTTTAATTGCAG

CTTATAATGGTTACAAATAAAGCAATAGCATCACAAATTTCACAAATAAAGCATTTTTTCACTGCATTCTAGTTGTGGTTTGTCCAA

ACTCATCAATGTATCTTAACGCGTAAATTGTAAGCGTTAATATTTTGTTAAAATTCGCGTTAAATTTTGTTAAATCAGCTCATTTTT

TAACCAATAGGCCGAAATCGGCAAAATCCCTTATAAATCAAAAGAATAGACCGAGATAGGGTTGAGTGTTGTTCCAGTTTGGAACAAG

AGTCCACTATTAAAGAACGTGGACTCCAACGTCAAAGGGCGAAAAACCGTCTATCAGGGCGATGGCCCACTACGTGAACCATCACCCT

AATCAAGTTTTTTGGGGTCGAGGTGCCGTAAAGCACTAAATCGGAACCCTAAAGGGAGCCCCCGATTTAGAGCTTGACGGGGAAAGCC

GGCGAACGTGGCGAGAAAGGAAGGGAAGAAAGCGAAAGGAGCGGGCGCTAGGGCGCTGGCAAGTGTAGCGGTCACGCTGCGCGTAACC

ACCACACCCGCCGCGCTTAATGCGCCGCTACAGGGCGCGTCAGGTGGCACTTTTCGGGGAAATGTGCGCGGAACCCCTATTTGTTTAT

TTTTCTAAATACATTCAAATATGTATCCGCTCATGAGACAATAACCCTGATAAATGCTTCAATAATATTGAAAAAGGAAGAGTCCTGA

GGCGGAAAGAACCAGCTGTGGAATGTGTGTCAGTTAGGGTGTGGAAAGTCCCCAGGCTCCCCAGCAGGCAGAAGTATGCAAAGCATGC

ATCTCAATTAGTCAGCAACCAGGTGTGGAAAGTCCCCAGGCTCCCCAGCAGGCAGAAGTATGCAAAGCATGCATCTCAATTAGTCAGC

AACCATAGTCCCGCCCCTAACTCCGCCCATCCCGCCCCTAACTCCGCCCAGTTCCGCCCATTCTCCGCCCCATGGCTGACTAATTTTT

TTTATTTATGCAGAGGCCGAGGCCGCCTCGGCCTCTGAGCTATTCCAGAAGTAGTGAGGAGGCTTTTTTGGAGGCCTAGGCTTTTGCA

AAGATCGATCAAGAGACAGGATGAGGATCGTTTCGCATGATTGAACAAGATGGATTGCACGCAGGTTCTCCGGCCGCTTGGGTGGAGA

GGCTATTCGGCTATGACTGGGCACAACAGACAATCGGCTGCTCTGATGCCGCCGTGTTCCGGCTGTCAGCGCAGGGGCGCCCGGTTCT

TTTTGTCAAGACCGACCTGTCCGGTGCCCTGAATGAACTGCAAGACGAGGCAGCGCGGCTATCGTGGCTGGCCACGACGGGCGTTCCT

TGCGCAGCTGTGCTCGACGTTGTCACTGAAGCGGGAAGGGACTGGCTGCTATTGGGCGAAGTGCCGGGGCAGGATCTCCTGTCATCTC

ACCTTGCTCCTGCCGAGAAAGTATCCATCATGGCTGATGCAATGCGGCGGCTGCATACGCTTGATCCGGCTACCTGCCCATTCGACCA

CCAAGCGAAACATCGCATCGAGCGAGCACGTACTCGGATGGAAGCCGGTCTTGTCGATCAGGATGATCAAGAGCATCAGGGGCTCGCG

CCAGCCGAACTGTTCGCCAGGCTCAAGGCGAGCATGCCCGACGGCGAGGATCTCGTCGTGACCCATGGCGATGCCTGCTTGCCGAATA

TCATGGTGGAAAATGGCCGCTTTTCTGGATTCATCGACTGTGGCCGGCTGGGTGTGGCGGACCGCTATCAGGACATAGCGTTGGCTAC

CCGTGATATTGCTGAAGAGCTTGGCGGCGAATGGGCTGACCGCTTCCTCGTGCTTTACGGTATCGCCGCTCCCGATTCGCAGCGCATC

GCCTTCTATCGCCTTCTTGACGAGTTCTTCTGAGCGGGACTCTGGGGTTCGAAATGACCGACCAAGCGACGCCCAACCTGCCATCACG

AGATTTCGATTCCACCGCCGCCTTCTATGAAAGGTTGGGCTTCGGAATCGTTTTCCGGGACGCCGGCTGGATGATCCTCCAGCGCGGG

GATCTCATGCTGGAGTTCTTCGCCCACCCTAGGGGGAGGCTAACTGAAACACGGAAGGAGACAATACCGGAAGGAACCCGCGCTATGA

CGGCAATAAAAAGACAGAATAAAACGCACGGTGTTGGGTCGTTTGTTCATAAACGCGGGGTTCGGTCCCAGGGCTGGCACTCTGTCGA

TACCCCACCGAGACCCCATTGGGGCCAATACGCCCGCGTTTCTTCCTTTTCCCCACCCCACCCCCCAAGTTCGGGTGAAGGCCCAGGG

CTCGCAGCCAACGTCGGGGCGGCAGGCCCTGCCATAGCCTCAGGTTACTCATATATACTTTAGATTGATTTAAAACTTCATTTTTAAT

TTAAAAGGATCTAGGTGAAGATCCTTTTTGATAATCTCATGACCAAAATCCCTTAACGTGAGTTTTCGTTCCACTGAGCGTCAGACCC

CGTAGAAAAGATCAAAGGATCTTCTTGAGATCCTTTTTTTCTGCGCGTAATCTGCTGCTTGCAAACAAAAAAACCACCGCTACCAGCG

GTGGTTTGTTTGCCGGATCAAGAGCTACCAACTCTTTTTCCGAAGGTAACTGGCTTCAGCAGAGCGCAGATACCAAATACTGTCCTTC

TAGTGTAGCCGTAGTTAGGCCACCACTTCAAGAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGATAAGGCGCAGCGGTCGGGCTGAACGGGGGT

TCGTGCACACAGCCCAGCTTGGAGCGAACGACCTACACCGAACTGAGATACCTACAGCGTGAGCTATGAGAAAGCGCCACGCTTCCCG

AAGGGAGAAAGGCGGACAGGTATCCGGTAAGCGGCAGGGTCGGAACAGGAGAGCGCACGAGGGAGCTTCCAGGGGGAAACGCCTGGTA

TCTTTATAGTCCTGTCGGGTTTCGCCACCTCTGACTTGAGCGTCGATTTTTGTGATGCTCGTCAGGGGGCGGAGCCTATGGAAAAAC

GCCAGCAACGCGGCCTTTTTACGGTTCCTGGCCTTTTGCTGGCCTTTTGCTCACATGTTCTTTCCTGCGTTATCCCCTGATTCTGTGG
```

```
ATAACCGTATTACCGCCATGCATTAGTTATTAATAGTAATCAATTACGGGGTCATTAGTTCATAGCCCATATAGGAGTTCCGCGTTAC

ATAACTTACGGTAAATGGCCCGCCTGGCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGCAGTACATCAAGTGTATCATATGCCAA

GTACGCCCCCTATTGACGTCAATGACGGTAAATGGCCCGCCTGGCATTATGCCCAGTACATGACCTTATGGGACTTTCCTACTTGGCA

GTACATCTACGTATTAGTCATCGCTATTACCATGGTGATGCGGTTTTGGCAGTACATCAATGGGCGTGGATAGCGGTTTGACTCACGG

GGATTTCCAAGTCTCCACCCCATTGACGTCAATGGGAGTTTGTTTTGGCACCAAAATCAACGGGACTTTCCAAAATGTCGTAACAACT

CCGCCCCATTGACGCAAATGGGCGGTAGGCGTGTACGGTGGGAGGTCTATATAAGCAGAGCTGGTTTAGTGAACCGTATGGCGGATGT

GTGACATACACGACGCCAAAAGATTTTGTTCCAGCTCCTGCCACCTCCGCTACGCGAGAGATTAACCACCCACGATGGCCGCCAAAGT

GCATGTTGATATTGAGGCTGACAGCCCATTCATCAAGTCTTTGCAGAAGGCATTTCCGTCGTTCGAGGTGGAGTCATTGCAGGTCACA

CCAAATGACCATGCAAATGCCAGAGCATTTTCGCACCTGGCTACCAAATTGATCGAGCAGGAGACTGACAAAGACACACTCATCTTGG

ATATCGGCAGTGCGCCTTCCAGGAGAATGATGTCTACGCACAAATACCACTGCGTATGCCCTATGCGCAGCGCAGAAGACCCCGAAAG

GCTCGTATGCTACGCAAAGAAACTGGCAGCGGCCTCCGAGAAGGTGCTGGATAGAGAGATCGCAGGAAAAATCACCGACCTGCAGACC

GTCATGGCTACGCCAGACGCTGAATCTCCTACCTTTTGCCTGCATACAGACGTCACGTGTCGTACGGCAGCCGAAGTGGCCGTATACC

AGGACGTGTATGCTGTACATGCACCAACATCGCTGTACCATCAGGCGATGAAAGGTGTCAGAACGGCGTATTGGATTGGGTTTGACAC

CACCCCGTTTATGTTTGACGCGCTAGCAGGCGCGTATCCAACCTACGCCACAAACTGGGCCGACGAGCAGGTGTTACAGGCCAGGAAC

ATAGGACTGTGTGCAGCATCCTTGACTGAGGGAAGACTCGGCAAACTGTCCATTCTCCGCAAGAAGCAATTGAAACCTTGCGACACAG

TCATGTTCTCGGTAGGATCTACATTGTACACTGAGAGCAGAAAGCTACTGAGGAGCTGGCACTTACCCTCCGTATTCCACCTGAAAGG

TAAACAATCCTTTACCTGTAGGTGCGATACCATCGTATCATGTGAAGGGTACGTAGTTAAGAAAATCACTATGTGCCCCGGCCTGTAC

GGTAAAACGGTAGGGTACGCCGTGACGTATCACGCGGAGGGATTCCTAGTGTGCAAGACCACAGACACTGTCAAAGGAGAAAGAGTCT

CATTCCCTGTATGCACCTACGTCCCCTCAACCATCTGTGATCAAATGACTGGCATACTGGCGACCGACATCACACCGGAGGACGCACA

GAAGTTGTTAGTGGGATTGAATCAGAGGATAGTTGTGAACGGAAGAACACAGCGAAACACTAACACGATGAAGAACTATCTGCTTCCG

ATTGTGGCCGTCGCATTTAGCAAGTGGGCGAGGGAATACAAGGCAGACCTTGATGATGAAAAACCTCTGGGTGTCCGAGAGAGGTCAC

TTACTTGCTGCTGCTTGTGGGCATTTAAAACGAGGAAGATGCACACCATGTACAAGAAACCAGACACCCAGACAATAGTGAAGGTGCC

TTCAGAGTTTAACTCGTTCGTCATCCCGAGCCTATGGTCTACAGGCCTCGCAATCCCAGTCAGATCACGCATTAAGATGCTTTTGGCC

AAGAAGACCAAGCGAGAGTCAATACCTGTTCTCGACGCGTCGTCAGCCAGGGATGCTGAACAAGAGGAGAAGGAGAGGTTGGAGGCCG

AGCTGACTAGAGAAGCCTTACCACCCCTCGTCCCCACCGCGCCGGCGGAGACGGGAGTCGTCGACGTCGACGTTGAAGAACTAGAGTA

TCACGCAGGTGCAGGGGTCGTGGAAACACCTCGCAGCGCGTTGAAAGTCACCGCACAGCCGAACGGCGTACTACTAGGAAATTACGTA

GTTCTGTCCCCGCAGACCGTGCTCAAGAGCTCCAAGTTGGCCCCCGTGCACCCTCTAGCAGAGCAGGTGAAAATAATAACACATAACG

GGAGGGCCGGCCGTTACCAGGTCGACGGATATGACGGCAGGGTCCTACTACCATGTGGATCGGCCATTCCGGTCCCTGAGTTTCAAGC

TTTGAGCGAGAGCGCCACTATGGTGTACAACGAAAGGGAGTTCGTCAACAGGAAACTATACCATATTGCCGTTCACGGACCGTCGCTG

AACACCGACGAGGAGAACTACGAGAAAGTCAGAGCTGAAAGAACTGACGCCGAGTACGTGTTCGACGTAGATAAAAAATGCTGCGT

CAAGAGAGAGGAAGCGTCGGGTTTGGTGTTGGTGGGAGAGCTAACCAACCCCCCGTTCCATGAATTCGCCTACGAAGGGCTGAAGATC

AGGCCGTCGGCACCCATATAAGACTACAGTAGTAGGAGTCTTTGGGGTTCCGGGATCAGGCAAGTCTGCTATTATTAAGAGCCTCGTGA

CCAAACACGATCTGGTCACCAGCGGCAAGAAGGAGAACTGCCAGGAAATAGTCAACGACGTGAAGAAGCACCGCGGACTGGACATCCA

GGCAAAAACAGTGGACTCCATCCTGCTAAACGGGTGTCGTCGTGCCGTGGACATCCTATATGTGGACGAGGCTTTCGCTTGCCATTCC

GGTACTCTGCTAGCCCTAATTGCTCTTGTTAAACCTCGGAGCAAAGTGGTGTTATGCGGAGACCCCAAGCAATGCGGATTCTTCAATA

TGATGCAGCTTAAGGTGAACTTCAACCACAACATCTGCACTGAAGTATGTCATAAAAGTATATCCAGACGTTGCACGCGTCCAGTCAC

GGCCATCGTGTCTACATTGCACTACGGAGGCAAGATGCGCACGACCAACCCGTGCAACAAACCCATAATCATAGCACACCACAGGACA

GACCAAGCCCAAGCCAGGAGACATCGTGTTAACATGCTTCCGAGGCTGGGTAAAGCAGCTGCAGTTGGACTACCGTGGACACGAAGTC

ATGACAGCAGCAGCATCTCAGGGCCTCACCCGCAAAGGGGTATACGCCGTAAGGCAGAAGGTGAATGAAAATCCCTTGTATGCCCCTG

CGTCGGAGCACGTGAATGTACTGCTGACGCGCACTGAGGATAGGCTGGTGTGGAAAACGCTGGCCGGCGATCCCTGGATTAAGGTCCT
```

-continued

```
ATCAAACATTCCACAGGGTAACTTTACGGCCACATTGGAAGAATGGCAAGAAGAACACGACAAAATAATGAAGGTGATTGAAGGACCG

GCTGCGCCTGTGGACGCGTTCCAGAACAAAGCGAACGTGTGTTGGGCGAAAAGCCTGGTGCCTGTCCTGGACACTGCCGGAATCAGAT

TGACAGCAGAGGAGTGGAGCACCATAATTACAGCATTTAAGGAGGACAGAGCTTACTCTCCAGTGGTGGCCTTGAATGAAATTTGCAC

CAAGTACTATGGAGTTGACCTGGACAGTGGCCTGTTTTCTGCCCCGAAGGTGTCCCTGTATTACGAGAACAACCACTGGGATAACAGA

CCTGGTGGAAGGATGTATGGATTCAATGCCGCAACAGCTGCCAGGCTGGAAGCTAGACATACCTTCCTGAAGGGGCAGTGGCATACGG

GCAAGCAGGCAGTTATCGCAGAAAGAAAAATCCAACCGCTTTCTGTGCTGGACAATGTAATTCCTATCAACCGCAGGCTGCCGCACGC

CCTGGTGACTGAGTACAAGACGGTTAAAGGCAGTAGGGTTGAGTGGCTGGTCAATAAAGTAAGAGGGTACCACGTCCTGCTGGTGAGT

GAGTACAACCTGGCTTTGCCTCGACGCAGGGTCACTTGGTTGTCACCGCTGAATGTCACAGGCGCCGATAGGTGCTACGACCTAAGTT

TAGGACTGCCGGCTGACGCCGGCAGGTTCGACTTGGTCTTTGTGAACATTCACACGGAATTCAGAATCCACCACTACCAGCAGTGTGT

CGACCACGCCATGAAGCTGCAGATGCTTGGGGGAGATGCGCTACGACTGCTAAAACCCGGCGGCAGCCTCTTGATGAGAGCTTACGGA

TACGCCGATAAAATCAGCGAAGCCGTTGTTTCCTCCTTAAGCAGAAAGTTCTCGTCTGCAAGAGTGTTGCGCCCGGATTGTGTCACCA

GCAATACAGAAGTGTTCTTGCTGTTCTCCAACTTTGACAACGGAAAGAGACCCTCTACGCTACACCAGATGAATACCAAGCTGAGTGC

CGTGTATGCCGGAGAAGCCATGCACACGGCCGGGTGTGCACCATCCTACAGAGTTAAGAGAGCAGACATAGCCACGTGCACAGAAGCG

GCTGTGGTTAACGCAGCTAACGCCCGTGGAACTGTAGGGGATGGCGTATGCAGGGCCGTGGCGAAGAAATGGCCGTCAGCCTTTAAGG

GAGGAAGCAACACCAGTGGGCACAATTAAAACAGTCATGTGCGGCTCGTACCCCGTCATCCACGCTGTAGCGCCTAATTTCTCTGCCA

CGACTGAAGCGGAAGGGGACCGCGAATTGGCCGCTGTCTACCGGGCAGTGGCCGCCGAAGTAAACAGACTGTCACTGAGCAGCGTAGC

CATCCCGCTGCTGTCCACAGGAGTGTTCAGCGGCGGAAGAGATAGGCTGCAGCAATCCCTCAACCATCTATTCACAGCAATGGACGCC

ACGGACGCTGACGTGACCATCTACTGCAGAGACAAAAGTTGGGAGAAGAAAATCCAGGAAGCCATAGACACGAGGACGGCTGTGGAGT

TGCTCAATGATGACGTGGAGCTGACCACAGACTTGGTGAGAGTGCACCCGGACAGCAGCCTGGTGGGTCGTAAGGGCTACAGTACCAC

TGACGGGTCGCTGTACTCGTACTTTGAAGGTACGAAATTCAACCAGGCTGCTATTGATATGGCAGAGATACTGACGTTGTGGCCCAGA

CTGCAAGAGGCAAACGAACAGATATGCCTATACGCGCTGGGCGAAACAATGGACAACATCAGATCCAAATGTCCGGTGAACGATTCCG

ATTCATCAACACCTCCCAGGACAGTGCCCTGCCTGTGCCGCTACGCAATGACAGCAGAACGGATCACCCGCCTTAGGTCACACCAAGT

TAAAAGCATGGTGGTTTGCTCATCTTTTCCCCTCCCGAAATACCATGTAGATGGGGTGCAGAAGGTAAAGTGCGAGAAGGTTCTCCTG

TTCGACCCGACGGTACCTTCAGTGGTTAGTCCGCGGAAGTATGCCGCATCTACGACGGACCACTCAGATCGGTCGTTACGAGGGTTTG

ACTTGGACTGGACCACCGACTCGTCTTCCACTGCCAGCGATACCATGTCGCTACCCAGTTTGCAGTCGTGTGACATCGACTCAGATCT

ACGAGCCAATGGCTCCCATAGTAGTGACGGCTGACGTACACCCTGAACCCGCAGGCATCGCGGACCTGGCGGCAGATGTGCATCCTGA

ACCCGCAGACCATGTGGACCTCGAGAACCCGATTCCTCCACCGCGCCCGAAGAGAGCTGCATACCTTGCCTCCCGCGCGGCGGAGCGA

CCGGTGCCGGCGCCGAGAAAGCCGACGCCTGCCCCAAGGACTGCGTTTAGGAACAAGCTGCCTTTGACGTTCGGCGACTTTGACGAGC

ACGAGGTCGATGCGTTGGCCTCCGGGATTACTTTCGGAGACTTCGACGACGTCCTGCGACTAGGCCGCGCGGGTGCATATATTTTCTC

CTCGGACACTGGCAGCGGACATTTACAACAAAAATCCGTTAGGCAGCACAATCTCCAGTGCGCACAACTGGATGCGGTCGAGGAGGAG

AAAATGTACCCGCCAAAATTGGATACTGAGAGGGAGAAGCTGTTGCTGCTGAAAATGCAGATGCACCCATCGGAGGCTAATAAGAGTC

GATACCAGTCTCGCAAAGTGGAGAACATGAAAGCCACGGTGGTGGACAGGCTCACATCGGGGGCCAGATTGTACACGGGAGCGGACGT

AGGCCGCATACCAACATACGCGGTTCGGTACCCCCGCCCCGTGTACTCCCCTACCGTGATCGAAAGATTCTCAAGCCCCGATGTAGCA

ATCGCAGCGTGCAACGAATACCTATCCAGAAATTACCCAACAGTGGCGTCGTACCAGATAACAGATGAATACGACGCATACTTGGACA

TGGTTGACGGGTCGGATAGTTGCTTGGACAGAGCGACATTCTGCCCGGCGAAGCTCCGGTGCTACCCGAAACATCATGCGTACCACCA

GCCGACTGTACGCAGTGCCGTCCCGTCACCCTTTCAGAACACACTACAGAGCGTGCTAGCGGCCGCCACCAAGAGAAACTGCAACGTC

ACGCAAATGCGAGAACTACCCACCATGGACTCGGCAGTGTTCAACGTGGAGTGCTTCAAGCGCTATGCCTGCTCCGGAGAATATTGGG

AAGAATATGCTAAACAACCTATCCGGATAACCACTGAGAACATCACTACCTATGTGACCAAATTGAAAGGCCCGAAAGCTGCTGCCTT

GTTCGCTAAGACCCACAACTTGGTTCCGCTGCAGGAGGTTCCCATGGACAGATTCACGGTCGACATGAAACGAGATGTCAAAGTCACT

CCAGGGACGAAACACACAGAGGAAAGACCCAAAGTCCAGGTAATTCAAGCAGCGGAGCCATTGGCGACCGCTTACCTGTGCGGCATCC
```

-continued

```
ACAGGGATTAGTAAGGAGACTAAATGCTGTGTTACGCCCTAACGTGCACACATTGTTTGATATGTCGGCCGAAGACTTTGACGCGATC
ATCGCCTCTCACTTCCACCCAGGAGACCCGGTTCTAGAGACGGACATTGCATCATTCGACAAAAGCCAGGACGACTCCTTGGCTCTTA
CAGGTTTAATGATCCTCGAAGATCTAGGGGTGGATCAGTACCTGCTGGACTTGATCGAGGCAGCCTTTGGGGAAATATCCAGCTGTCA
CCTACCAACTGGCACGCGCTTCAAGTTCGGAGCTATGATGAAATCGGGCATGTTTCTGACTTTGTTTATTAACACTGTTTTGAACATC
ACCATAGCAAGCAGGGTACTGGAGCAGAGACTCACTGACTCCGCCTGTGCGGCCTTCATCGGCGACGACAACATCGTTCACGGAGTGA
TCTCCGACAAGCTGATGGCGGAGAGGTGCGCGTCGTGGGTCAACATGGAGGTGAAGATCATTGACGCTGTCATGGGCGAAAAACCCCC
ATATTTTTGTGGGGGATTCATAGTTTTTGACAGCGTCACACAGACCGCCTGCCGTGTTTCAGACCCACTTAAGCGCCTGTTCAAGTTG
GGTAAGCCGCTAACAGCTGAAGACAAGCAGGACGAAGACAGGCGACGAGCACTGAGTGACGAGGTTAGCAAGTGGTTCCGGACAGGCT
TGGGGGCCGAACTGGAGGTGGCACTAACATCTAGGTATAAGGTAGAGGGCTGCAAAAGTATCCTCATAGCCATGGCCACCTTGGCGAG
GGACATTAAGGCGTTTAAGAAATTGAGAGGACCTGTTATACACCTCTACGGCGGTCCTAGATTGGTGCGTTAATACACAGAATTCTGA
TTGGATCCTCGAGGAATTCTGACACTATGAAGTGCCTTTTGTACTTAGCCTTTTTATTCATTGGGGTGAATTGCAAGTTCACCATAGT
TTTTCCACACAACCAAAAGGAAACTGGAAAAATGTTCCTTCTAATACCATTATTGCCCGTCAAGCTCAGATTTAAATTGGCATGATG
ACTTAATAGGCACAGCCTTACAAGTCAAAATGCCCAAGAGTCACAAGGCTATTCAAGCAGACGGTTGGATGTGTCATGCTTCCAAATG
GGTCACTACTTGTGACTTCCGCTGGTATGGACCGAAGTATATAACACATTCCATCCGATCCTTCACTCCATCTGTAGAACAATGCAAG
GAAAGCATTGAACAAACGAAACAAGGAACTTGGCTGAATCCAGGCTTCCCTCCTCAAGTTGTGGATATGCAACTGTGACGGATGCCGA
AGCAGTGATTGTCCAGGTGACTCCTCACCATGTGCTGGTTGATGAATACACAGGAGAATGGGTTGATTCACAGTTCATCAACGGAAAA
TGCAGCAATTACATATGCCCCACTGTCCATAACTCTACAACCTGGCATTCTGACTATAAGGTCAAAGGGCTATGTGATTCTAACCTCA
TTTCCATGGACATCACCTTCTTCTCAGAGGACGGAGAGCTATCATCCCTGGGAAGGAGGGCACAGGGTTCAGAAGTAACTACTTTGC
TTATGAAACTGGAGGCAAGGCCTGCAAAATGCAATACTGCAAGCATTGGGGAGTCAGACTCCCATCAGGTGTCTGGTTCGAGATGGCT
GATAAGGATCTCTTTGCTGCAGCCAGATTCCCTGAATGCCCAGAAGGGTCAAGTATCTCTGCTCCATCTCAGACCTCAGTGGATGTAA
GTCTAATTCAGGACGTTGAGAGGATCTTGGATTATTCCCTCTGCCAAGAAACCTGGAGCAAAATCAGAGCGGGTCTTCCAATCTCTCC
AGTGGATCTCAGCTATCTTGCTCCTAAAAACCCAGGAACCGGTCCTGCTTTCACCATAATCAATGGTACCCTAAAATACTTTGAGACC
AGATACATCAGAGTCGATATTGCTGCTCCAATCCTCTCAAGAATGGTCGGAATGATCAGTGGAACTACCACAGAAAGGGAACTGTGGG
ATGACTGGGCACCATATGAAGACGTGGAAATTGGACCCAATGGAGTTCTGAGGACCAGTTCAGGATATAAGTTTCCTTTATACATGAT
TGGACATGGTATGTTGGACTCCGATCTTCATCTTAGCTCAAAGGCTCAGGTGTTCGAACATCCTCACATTCAAGACGCTGCTTCGCAA
CTTCCTGATGATGAGAGTTTATTTTTTGGTGATACTGGGCTATCCAAAAATCCAATCGAGCTTGTAGAAGGTTGGTTCAGTAGTTGGA
AAAGCTCTATTGCCTCTTTTTTCTTTATCATAGGGTTAATCATTGGACTATTCTTGGTTCTCCGAGTTGGTATCCATCTTTGCATTAA
ATTAAAGCACACCAAGAAAAGACAGATTTATACAGACATAGAGATGAACCGACTTGGAAAGTAACTCAAATCCTGCACAACAGATTCT
TCATGTTTGGACCAAATCAACTTGTGATACCATGCTCAAAGAGGCCTCAAACCATAACTGTATAACTTGTAACAAAGCGCAACAAGAC
CTGCGCAATTGGCCCCGTGGTCCGCCTCACGGAAACTCGGGGCAACTCATATTGACACATTAATTGGCAATAATTGGAAGCTTACATA
AGCTTAATTCGACGAATAATTGGATTTTTATTTTATTTTGCAATTGGTTTTTAATATTTCCAAAAAAAAAAAAAAAAAAAAAAAAAAA
AAAAAAAAAAAAAAAAAAAAAAAAAAAAAAAAAAAAAAAA-3'
```

What is claimed:

1. A high titer hybrid-virus vector comprising a DNA sequence comprising a promoter sequence operably linked to a DNA sequence encoding alphavirus non-structural protein nucleotide sequences, operably linked to an alphavirus subgenomic RNA promoter, operably linked to a 2A DNA encoding a 2A peptide, which is in turn operably linked to a vesicular stomatitis virus (VSV) G DNA encoding a VSV G protein, wherein the alphavirus non-structural protein nucleotide sequences comprise a T-5930-C mutation and wherein the vector comprises at least one other mutation selected from the group consisting of G-4700-A, A-5424-G, G-5434-A, T-5825-C, A-6047-G, G-6783-A, G-6963-A, G-7834-A, T-8859-A, T-8864-C, G-9211-A, A-10427-G, G-11560-A, A-11871-G and T-11978-C, wherein the nucleotide positions are numbered based on the numbering of the nucleotides in SEQ ID NO:1, wherein the vector lacks functional nucleotide sequences which encode alphavirus structural proteins, further wherein when the vector is propagated in a cell culture, titers of more than $5 \times 10^7$ plaque forming units (pfu) per ml of virus like vesicles (VLVs) are obtained.

2. The high titer hybrid-virus vector of claim 1, wherein the alphavirus is Semliki Forest virus (SFV).

3. The high titer hybrid-virus vector of claim 1, wherein the subgenomic RNA promoter is an Semliki Forest virus (SFV) promoter.

4. The high titer hybrid-virus vector of claim 1, wherein the 2A DNA is Thosea asigna virus DNA and encodes a T2A peptide.

5. Virus like vesicles (VLVs) containing a replicon RNA generated by the high titer hybrid-virus vector of claim 1.

6. The high titer hybrid-virus vector of claim 1, wherein the promoter sequence is a constitutive promoter.

7. The high titer hybrid-virus vector of claim 6, wherein the promoter sequence is the cytomegalovirus immediate early promoter.

8. The high titer hybrid-virus vector of claim 1, wherein titers of at least $1 \times 10^8$ pfu/ml of VLVs are obtained.

9. The high titer hybrid virus vector of claim 1, wherein DNA encoding at least one heterologous protein is inserted between the alphavirus subgenomic RNA promoter, and the 2A DNA.

10. The high titer hybrid-virus vector of claim 9, wherein the at least one heterologous protein is associated with a disease selected from the group consisting of infectious disease, malignant disease and autoimmune disease.

11. The high titer hybrid-virus vector of claim 10, wherein the infectious disease is caused by a prokaryote selected from the group consisting of *Escherichia, Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasteurella, Moraxella, Acinetobacter, Erysipelothrix, Branhamella, Actinobacillus, Streptobacillus, Listeria, Calymmatobacterium, Brucella, Bacillus, Clostridium, Treponema, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Coxiella, Borrelia* and *Mycoplasma.*

12. The high titer hybrid-virus vector of claim 10, wherein the infectious disease is caused by a virus selected from the group consisting of human immunodeficiency virus (HIV), hepatitis A virus (HAV), hepatitis B (HBV), hepatitis C (HCV), any other hepatitis-associated virus, human papillomavirus (HPV) and especially high-risk oncogenic human papillomavirus types, Kaposi's Sarcoma-Associated Herpesvirus (KSHV) (also known as Human Herpesvirus-8 (HHV-8)), Herpes Simplex virus (HSV) (any subtype), Respiratory Syncytial Virus (RSV) and associated respiratory viruses, Influenza viruses, coronaviruses including SARS-associated Coronavirus (SARS-CoV), rhinovirus, adenovirus, SIV, rotavirus, human papilloma virus, arbovirus, measles virus, polio virus, rubella virus, mumps virus, papova virus, cytomegalovirus, varicella-zoster virus, varicella virus, huntavirus and any emergent virus, in particular Ebola virus, Marburg virus, West Nile virus (WNV), St Louis Encephalitis virus (SLEV), Rift Valley Fever virus (RVFV) and other members of the Bunyaviridae.

13. The high titer hybrid-virus vector of claim 10, wherein the infectious disease is caused by a protozoan selected from the group consisting of apicomplexans and trypanosomatids.

14. The high titer hybrid-virus vector of claim 10, wherein the malignant disease is a cancer selected from the group consisting of Acute and Chronic Myelogenous Leukemia (AML, CML), Follicular Non-Hodgkins lymphoma, malignant melanoma, Hairy Cell leukaemia, multiple myeloma, carcinoid tumors with carcinoid syndrome and liver and lymph node metastases, AIDS related Kaposi's sarcoma, renal cell carcinoma, adenocarcinoma of the large bowel, squamous cell carcinoma of the head and neck, colon cancer, lung cancer, breast cancer, stomach cancer, prostate cancer, and endometrial cancer.

15. The high titer hybrid-virus vector of claim 10, wherein the autoimmune disease is selected from the group consisting of Addison's disease, Celiac disease, Dermatomyositis, Graves' disease, Hashimoto's thyroiditis, Multiple sclerosis, Myasthenia gravis, Pernicious anemia, Reactive arthritis, Rheumatoid arthritis, Sjogren syndrome, Systemic lupus erythematosus and Type I diabetes.

16. A composition comprising virus like vesicles (VLVs) produced by the high titer hybrid-virus vector of claim 1.

17. A composition comprising virus like vesicles (VLVs) produced by the high titer hybrid-virus vector of claim 9.

18. The composition of claim 17, wherein the heterologous protein is associated with a disease selected from the group consisting of infectious disease, malignant disease and autoimmune disease.

19. A method of immunizing a subject against a heterologous protein, the method comprising administering to the subject a composition comprising at least $10^7$ pfu/ml of the VLVs of claim 17, wherein expression of the heterologous protein induces an immune response in the subject.

20. The method of claim 19, wherein the heterologous protein is associated with a disease selected from the group consisting of infectious disease, malignant disease and autoimmune disease.

21. A method of treating and/or preventing a disease in a subject, the method comprising administering a therapeutically effective amount of the composition of claim 15 to a subject in need of such treatment.

22. The method of claim 21, wherein the disease is a disease selected from the group consisting of infectious disease, malignant disease and autoimmune disease.

23. A method of vaccinating a subject, the method comprising administering to the subject a pharmaceutically acceptable amount of the composition of claim 17, wherein administration of the composition elicits an immune response in the subject.

24. The method of claim 23, wherein the composition is administered prophylactically to the subject.

25. The method of claim 24, wherein the composition is administered therapeutically to the subject.

26. The method of claim 23, wherein the composition is administered in combination with an adjuvant.

27. The method of claim 26, wherein the adjuvant is selected from the group consisting of Freund's complete adjuvant, Freund's incomplete adjuvant, Quil A, Detox, ISCOMs and squalene.

28. A method of generating a memory T cell immune response to a heterologous protein in a subject the method comprising the steps of: (a) administering the composition of claim 17 to a subject in an amount effective to elicit an immune response in the subject; (b) administering a second effective amount of the composition of claim 17 at a second, subsequent time period, wherein T memory cells directed against the heterologous protein are generated in the subject.

29. A method of generating an adaptive B cell immune response to a heterologous protein in a subject the method comprising the steps of: (a) administering the composition of claim 17 to a subject in an amount effective to elicit an immune response in the subject; (b) administering a second effective amount of the composition of claim 17 at a second, subsequent time period, wherein B memory cells directed against the heterologous protein are generated in the subject.

30. A protein expression system including a high titer hybrid-virus vector comprising a DNA sequence comprising a promoter sequence operably linked to a DNA sequence encoding alphavirus non-structural protein nucleotide sequences, operably linked to an alphavirus subgenomic RNA promoter, operably linked to a 2A DNA encoding a 2A peptide, which is in turn operably linked to a vesicular stomatitis virus (VSV) G DNA encoding a VSV G protein, wherein the SFV non-structural protein nucleotide sequences comprise a T-5930-C mutation and wherein the vector comprises at least one other mutation selected from the group consisting of G-4700-A, A-5424-G, G-5434-A, T-5825-C, A-6047-G, G-6783-A, G-6963-A, G-7834-A, T-8859-A, T-8864-C, G-9211-A, A-10427-G, G-11560-A, A-11871-G and T-11978-C, wherein the nucleotide positions are numbered based on the numbering of the nucleotides in SEQ ID NO:1, wherein the vector lacks functional nucleotide sequences which encode alphavirus structural proteins, further wherein when the vector is propagated in a cell culture, titers of more than $5\times10^7$ plaque forming units (pfu) per ml of virus like vesicles (VLVs) are obtained.

31. The protein expression system of claim 30, wherein the alphavirus is Semliki Forest virus (SFV).

32. The protein expression system of claim 30, wherein the subgenomic RNA promoter is from a Semliki Forest virus (SFV) promoter.

33. The protein expression system of claim 30, wherein the 2A DNA is Thosea asigna virus DNA and encodes a T2A peptide.

34. Virus like vesicles (VLVs) containing a replicon RNA generated by the high titer hybrid-virus vector of claim 30.

35. The protein expression system of claim 30, wherein the promoter sequence is a constitutive promoter.

36. The protein expression system of claim 35, wherein the promoter sequence is the cytomegalovirus immediate early promoter.

37. The protein expression system of claim 30, wherein titers of at least $1\times10^8$ pfu/ml of VLVs are obtained.

38. The protein expression system of claim 30, wherein DNA encoding at least one heterologous protein is inserted between the alphavirus subgenomic RNA promoter, and the 2A DNA.

39. A method of stabilizing the expression of a VSV G protein in VLVs, the method comprising operably linking an alphavirus non-structural protein nucleotide sequences to a 2A DNA encoding a 2A peptide, which is in turn operably linked to a DNA encoding a VSV G protein such that expression of the VLV G protein is maintained throughout replication of the VLVs, and further wherein the alphavirus non-structural protein nucleotide sequences comprise a T-5930-C mutation and wherein the VLVs comprise at least one other mutation selected from the group consisting of G-4700-A, A-5424-G, G-5434-A, T-5825-C, A-6047-G, G-6783-A, G-6963-A, G-7834-A, T-8859-A, T-8864-C, G-9211-A, A-10427-G, G-11560-A, A-11871-G and T-11978-C, wherein the nucleotide positions are numbered based on the numbering of the nucleotides in SEQ ID NO:1.

40. A method of stabilizing the expression of a heterologous protein in VLVs, the method comprising operably linking an alphavirus non-structural protein nucleotide sequences to a 2A DNA encoding a 2A peptide, which is in turn operably linked to a DNA encoding a heterologous protein, in turn operably linked to a VSV G protein such that expression of the heterologous protein is maintained throughout replication of the VLVs, and further wherein the alphavirus non-structural protein nucleotide sequences comprise a T-5930-C mutation and wherein the VLVs comprise at least one other mutation selected from the group consisting of G-4700-A, A-5424-G, G-5434-A, T-5825-C, A-6047-G, G-6783-A, G-6963-A, G-7834-A, T-8859-A, T-8864-C, G-9211-A, A-10427-G, G-11560-A, A-11871-G and T-11978-C, wherein the nucleotide positions are numbered based on the numbering of the nucleotides in SEQ ID NO:1.

41. The method of any of claims 19, 21, 23, 28 and 29, wherein the subject is a mammal.

42. The method of claim 41, wherein the mammal is a human.

43. An RNA virus like vesicle (VLV), having a titer of more than $5\times10^7$ plaque forming units (pfu), wherein the VLV lacks nucleotide sequences encoding SFV structural proteins and comprises nucleotide sequences encoding a VSV G protein and SFV non-structural proteins, wherein the VLV comprises a T-5930-C mutation and at least one other mutation selected from the group consisting of G-4700-A, A-5424-G, G-5434-A, T-5825-C, A-6047-G, G-6783-A, G-6963-A, G-7834-A, T-8859-A, T-8864-C, G-9211-A, A-10427-G, G-11560-A, A-11871-G and T-11978-C, wherein the nucleotide positions are numbered based on the numbering of the nucleotides in SEQ ID NO: 1.

* * * * *

UNITED STATES PATENT AND TRADEMARK OFFICE
CERTIFICATE OF CORRECTION

| | |
|---|---|
| PATENT NO. | : 10,435,712 B2 |
| APPLICATION NO. | : 15/305237 |
| DATED | : October 8, 2019 |
| INVENTOR(S) | : John Rose and Nina Rose |

Page 1 of 1

It is certified that error appears in the above-identified patent and that said Letters Patent is hereby corrected as shown below:

In the Specification

On Column 1, Lines 16-22, please replace the existing paragraph with the following paragraph:
-- STATEMENT REGARDING FEDERALLY SPONSORED RESEARCH OR DEVELOPMENT
This invention was made with government support under AI045510 and AI040357 awarded by National Institutes of Health. The government has certain rights in the invention. --

Signed and Sealed this
Eleventh Day of August, 2020

Andrei Iancu
*Director of the United States Patent and Trademark Office*

SEQUENCE LISTING

<160> NUMBER OF SEQ ID NOS: 2

<210> SEQ ID NO 1
<211> LENGTH: 13590
<212> TYPE: DNA
<213> ORGANISM: Artificial Sequence
<220> FEATURE:
<223> OTHER INFORMATION: Hybrid virus vector (pCMV-SFVG-p50R)

<400> SEQUENCE: 1

-continued

| | | | | | |
|---|---|---|---|---|---|
| ctagtgcatc | caaagaattc | aaaaagcttc | tcgagagtac | ttctagagcg | gccgcgcatc | 60 |
| gattttccac | ccgggtgggg | taccaggtaa | gtgtacccaa | ttcgccctat | agtgagtcgt | 120 |
| attacaattc | actggccgtc | gttttacaac | gtcgtgactg | ggaaaaccct | ggcgttaccc | 180 |
| aacttaatcg | ccttgcagca | catcccectt | cgccagctg | gcgtaatagc | gaagaggccc | 240 |
| gcaccgatcg | cccttcccaa | cagttgcgca | gcctgaatgg | cgaatggaga | tccaattttt | 300 |
| aagtgtataa | tgtgttaaac | tactgattct | aattgtttgt | gtattttaga | ttcacagtcc | 360 |
| caaggctcat | ttcaggcccc | tcagtcctca | cagtctgttc | atgatcataa | tcagccatac | 420 |
| cacatttgta | gaggttttac | ttgctttaaa | aaacctccca | cacctccccc | tgaacctgaa | 480 |
| acataaaatg | aatgcaattg | ttgttgttaa | cttgtttatt | gcagcttata | atggttacaa | 540 |
| ataaagcaat | agcatcacaa | atttcacaaa | taaagcattt | ttttcactgc | attctagttg | 600 |
| tggtttgtcc | aaactcatca | atgtatctta | acgcgtaaat | tgtaagcgtt | aatattttgt | 660 |
| taaaattcgc | gttaaatttt | tgttaaatca | gctcattttt | taaccaatag | gccgaaatcg | 720 |
| gcaaaatccc | ttataaatca | aagaataga | ccgagatagg | gttgagtgtt | gttccagttt | 780 |
| ggaacaagag | tccactatta | aagaacgtgg | actccaacgt | caaagggcga | aaaaccgtct | 840 |
| atcagggcga | tggcccacta | cgtgaaccat | caccctaatc | aagttttttg | gggtcgaggt | 900 |
| gccgtaaagc | actaaatcgg | aaccctaaag | ggagcccccg | atttagagct | tgacggggaa | 960 |
| agccggcgaa | cgtggcgaga | aaggaaggga | agaaagcgaa | aggagcgggc | gctagggcgc | 1020 |
| tggcaagtgt | agcggtcacg | ctgcgcgtaa | ccaccacacc | cgccgcgctt | aatgcgccgc | 1080 |
| tacagggcgc | gtcaggtggc | acttttcggg | gaaatgtgcg | cggaacccct | atttgtttat | 1140 |
| ttttctaaat | acattcaaat | atgtatccgc | tcatgagaca | ataaccctga | taaatgcttc | 1200 |
| aataatattg | aaaaaggaag | agtcctgagg | cggaaagaac | cagctgtgga | atgtgtgtca | 1260 |
| gttagggtgt | ggaaagtccc | caggctcccc | agcaggcaga | agtatgcaaa | gcatgcatct | 1320 |
| caattagtca | gcaaccaggt | gtggaaagtc | cccaggctcc | ccagcaggca | gaagtatgca | 1380 |
| aagcatgcat | ctcaattagt | cagcaaccat | agtcccgccc | ctaactccgc | ccatcccgcc | 1440 |
| cctaactccg | cccagttccg | cccattctcc | gccccatggc | tgactaattt | tttttattta | 1500 |
| tgcagaggcc | gaggccgcct | cggcctctga | gctattccag | aagtagtgag | gaggcttttt | 1560 |
| tggaggccta | ggcttttgca | aagatcgatc | aagagacagg | atgaggatcg | tttcgcatga | 1620 |
| ttgaacaaga | tggattgcac | gcaggttctc | cggccgcttg | ggtggagagg | ctattcggct | 1680 |
| atgactgggc | acaacagaca | atcggctgct | ctgatgccgc | cgtgttccgg | ctgtcagcgc | 1740 |
| aggggcgccc | ggttcttttt | gtcaagaccg | acctgtccgg | tgccctgaat | gaactgcaag | 1800 |
| acgaggcagc | gcggctatcg | tggctggcca | cgacgggcgt | tccttgcgca | gctgtgctcg | 1860 |
| acgttgtcac | tgaagcggga | agggactggc | tgctattggg | cgaagtgccg | gggcaggatc | 1920 |
| tcctgtcatc | tcaccttgct | cctgccgaga | aagtatccat | catggctgat | gcaatgcggc | 1980 |
| ggctgcatac | gcttgatccg | gctacctgcc | cattcgacca | ccaagcgaaa | catcgcatcg | 2040 |
| agcgagcacg | tactcggatg | gaagccggtc | ttgtcgatca | ggatgatcaa | gagcatcagg | 2100 |
| ggctcgcgcc | agccgaactg | ttcgccaggc | tcaaggcgag | catgcccgac | ggcgaggatc | 2160 |
| tcgtcgtgac | ccatggcgat | gcctgcttgc | cgaatatcat | ggtggaaaat | ggccgctttt | 2220 |
| ctggattcat | cgactgtggc | cggctgggtg | tggcggaccg | ctatcaggac | atagcgttgg | 2280 |
| ctacccgtga | tattgctgaa | gagcttggcg | gcgaatgggc | tgaccgcttc | ctcgtgcttt | 2340 |
| acggtatcgc | cgctcccgat | tcgcagcgca | tcgccttcta | tcgccttctt | gacgagttct | 2400 |

```
tctgagcggg actctggggt tcgaaatgac cgaccaagcg acgcccaacc tgccatcacg    2460
agatttcgat tccaccgccg ccttctatga aaggttgggc ttcggaatcg ttttccggga    2520
cgccggctgg atgatcctcc agcgcgggga tctcatgctg gagttcttcg cccacccatg    2580
ggggaggcta actgaaacac ggaaggagac aataccggaa ggaacccgcg ctatgacggc    2640
aataaaaaga cagaataaaa cgcacggtgt tgggtcgttt gttcataaac gcggggttcg    2700
gtcccagggc tggcactctg tcgataccc accgagaccc cattgggcc aatacgcccg     2760 cgtttcttcc ttttccccac cccacccccc aagttcgggt gaaggccag ggctcgcagc    2820 caacgtcggg gcggcaggcc ctgccatagc ctcaggttac tcatatatac tttagattga    2880
tttaaaactt catttttaat ttaaaaggat ctaggtgaag atcctttttg ataatctcat    2940
gaccaaaatc ccttaacgtg agttttcgtt ccactgagcg tcagacccg tagaaaagat     3000 caaaggatct tcttgagatc ctttttttct gcgcgtaatc tgctgcttgc aaacaaaaaa    3060
accaccgcta ccagcggtgg tttgtttgcc ggatcaagag ctaccaactc tttttccgaa    3120
ggtaactggc ttcagcagag cgcagatacc aaatactgtc cttctagtgt agccgtagtt    3180
aggccaccac ttcaagaact ctgtagcacc gcctacatac ctcgctctgc taatcctgtt    3240
accagtggct gctgccagtg gcgataagtc gtgtcttacc gggttggact caagacgata    3300
gttaccggat aaggcgcagc ggtcgggctg aacggggggt tcgtgcacac agcccagctt    3360
ggagcgaacg acctacaccg aactgagata cctacagcgt gagctatgag aaagcgccac    3420
gcttcccgaa gggagaaagg cggacaggta tccggtaagc ggcagggtcg gaacaggaga    3480
gcgcacgagg gagcttccag ggggaaacgc ctggtatctt tatagtcctg tcgggtttcg    3540
ccacctctga cttgagcgtc gatttttgtg atgctcgtca gggggcgga gcctatggaa     3600 aaacgccagc aacgcggcct ttttacggtt cctggccttt tgctggcctt tgctcacat     3660 gttctttcct gcgttatccc ctgattctgt ggataaccgt attaccgcca tgcattagtt    3720
attaatagta atcaattacg gggtcattag ttcatagccc atatatggag ttccgcgtta    3780
cataacttac ggtaaatggc ccgcctggct gaccgcccaa cgacccccgc ccattgacgt    3840
caataatgac gtatgttccc atagtaacgc caatagggac tttccattga cgtcaatggg    3900
tggagtattt acggtaaact gcccacttgg cagtacatca agtgtatcat atgccaagta    3960
cgccccctat tgacgtcaat gacggtaaat ggcccgcctg gcattatgcc cagtacatga    4020
ccttatggga ctttcctact tggcagtaca tctacgtatt agtcatcgct attaccatgg    4080
tgatgcggtt ttggcagtac atcaatgggc gtggatagcg gtttgactca cggggatttc    4140
caagtctcca ccccattgac gtcaatggga gtttgttttg gcaccaaaat caacgggact    4200
ttccaaaatg tcgtaacaac tccgccccat tgacgcaaat gggcggtagg cgtgtacggt    4260
gggaggtcta taagcaga gctggtttag tgaaccgtat ggcggatgtg tgacatacac     4320
gacgccaaaa gattttgttc cagctcctgc cacctccgct acgcgagaga ttaaccaccc    4380
acgatggccg ccaaagtgca tgttgatatt gaggctgaca gcccattcat caagtctttg    4440
cagaaggcat ttccgtcgtt cgaggtggag tcattgcagg tcacaccaaa tgaccatgca    4500
aatgccagag cattttcgca cctggctacc aaattgatcg agcaggagac tgacaaagac    4560
acactcatct tggatatcgg cagtgcgcct tccaggagaa tgatgtctac gcacaaatac    4620
cactgcgtat gccctatgcg cagcgcagaa gaccccgaaa ggctcgtatg ctacgcaaag    4680
aaactggcag cggcctccga gaaggtgctg gatagagaga tcgcaggaaa aatcaccgac    4740
```

```
ctgcagaccg tcatggctac gccagacgct gaatctccta ccttttgcct gcatacagac    4800
gtcacgtgtc gtacggcagc cgaagtggcc gtataccagg acgtgtatgc tgtacatgca    4860
ccaacatcgc tgtaccatca ggcgatgaaa ggtgtcagaa cggcgtattg gattgggttt    4920
gacaccaccc cgtttatgtt tgacgcgcta gcaggcgcgt atccaaccta cgccacaaac    4980
tgggccgacg agcaggtgtt acaggccagg aacataggac tgtgtgcagc atccttgact    5040
gagggaagac tcggcaaact gtccattctc cgcaagaagc aattgaaacc ttgcgacaca    5100
gtcatgttct cggtaggatc tacattgtac actgagagca gaaagctact gaggagctgg    5160
cacttaccct ccgtattcca cctgaaaggt aaacaatcct ttacctgtag gtgcgatacc    5220
atcgtatcat gtgaagggta cgtagttaag aaaatcacta tgtgccccgg cctgtacggt    5280
aaaacggtag ggtacgccgt gacgtatcac gcggagggat tcctagtgtg caagaccaca    5340
gacactgtca aaggagaaag agtctcattc cctgtatgca cctacgtccc ctcaaccatc    5400
tgtgatcaaa tgactggcat actggcgacc gacatcacac cggaggacgc acagaagttg    5460
ttagtgggat tgaatcagag gatagttgtg aacggaagaa cacagcgaaa cactaacacg    5520
atgaagaact atctgcttcc gattgtggcc gtcgcattta gcaagtgggc gagggaatac    5580
aaggcagacc ttgatgatga aaaacctctg ggtgtccgag agaggtcact tacttgctgc    5640
tgcttgtggg catttaaaac gaggaagatg cacaccatgt acaagaaacc agacacccag    5700
acaatagtga aggtgcctto agagtttaac tcgttcgtca tcccgagcct atggtctaca    5760
ggcctcgcaa tcccagtcag atcacgcatt aagatgcttt tggccaagaa gaccaagcga    5820
gagtcaatac ctgttctcga cgcgtcgtca gccaggatg ctgaacaaga ggagaaggag    5880
aggttggagg ccgagctgac tagagaagcc ttaccacccc tcgtcccac cgcgccggcg    5940 gagacgggag tcgtcgacgt cgacgttgaa gaactagagt atcacgcagg tgcagggtc    6000 gtggaaacac ctcgcagcgc gttgaaagtc accgcacagc cgaacggcgt actactagga    6060
aattacgtag ttctgtcccc gcagaccgtg ctcaagagct ccaagttggc ccccgtgcac    6120
cctctagcag agcaggtgaa aataataaca cataacggga gggccggccg ttaccaggtc    6180
gacggatatg acggcagggt cctactacca tgtggatcgg ccattccggt ccctgagttt    6240
caagctttga gcgagagcgc cactatggtg tacaacgaaa gggagttcgt caacaggaaa    6300
ctataccata ttgccgttca cggaccgtcg ctgaacaccg acgaggagaa ctacgagaaa    6360
gtcagagctg aaagaactga cgccgagtac gtgttcgacg tagataaaaa atgctgcgtc    6420
aagagagagg aagcgtcggg tttggtgttg gtgggagagc taaccaaccc cccgttccat    6480
gaattcgcct acgaagggct gaagatcagg ccgtcggcac catataagac tacagtagta    6540
ggagtctttg gggttccggg atcaggcaag tctgctatta ttaagagcct cgtgaccaaa    6600
cacgatctgg tcaccagcgg caagaaggag aactgccagg aaatagtcaa cgacgtgaag    6660
aagcaccgcg gactggacat ccaggcaaaa acagtggact ccatcctgct aaacgggtgt    6720
cgtcgtgccg tggacatcct atatgtggac gaggctttcg cttgccattc cggtactctg    6780
ctagccctaa ttgctcttgt taaacctcgg agcaaagtgg tgttatgcgg agaccccaag    6840
caatgcggat tcttcaatat gatgcagctt aaggtgaact tcaaccacaa catctgcact    6900
gaagtatgtc ataaaagtat atccagacgt tgcacgcgtc cagtcacggc catcgtgtct    6960
acattgcact acgaggcaa gatgcgcacg accaacccgt gcaacaaacc cataatcata    7020
gacaccacag gacagaccaa gcccaagcca ggagacatcg tgttaacatg cttccgaggc    7080
tgggtaaagc agctgcagtt ggactaccgt ggacacgaag tcatgacagc agcagcatct    7140
```

```
cagggcctca cccgcaaagg ggtatacgcc gtaaggcaga aggtgaatga aaatcccttg  7200
tatgcccctg cgtcggagca cgtgaatgta ctgctgacgc gcactgagga taggctggtg  7260
tggaaaacgc tggccggcga tccctggatt aaggtcctat caaacattcc acagggtaac  7320
tttacggcca cattggaaga atggcaagaa gaacacgaca aaataatgaa ggtgattgaa  7380
ggaccggctg cgcctgtgga cgcgttccag aacaaagcga acgtgtgttg ggcgaaaagc  7440
ctggtgcctg tcctggacac tgccggaatc agattgacag cagaggagtg gagcaccata  7500
attacagcat ttaaggagga cagagcttac tctccagtgg tggccttgaa tgaaatttgc  7560
accaagtact atggagttga cctggacagt ggcctgtttt ctgccccgaa ggtgtccctg  7620
tattacgaga caaccactg ggataacaga cctggtggaa ggatgtatgg attcaatgcc   7680
gcaacagctg ccaggctgga agctagacat accttcctga aggggcagtg gcatacgggc  7740
aagcaggcag ttatcgcaga aagaaaaatc caaccgcttt ctgtgctgga caatgtaatt  7800
cctatcaacc gcaggctgcc gcacgccctg gtgactgagt acaagacggt taaaggcagt  7860
agggttgagt ggctggtcaa taaagtaaga gggtaccacg tcctgctggt gagtgagtac  7920
aacctggctt tgcctcgacg cagggtcact tggttgtcac cgctgaatgt cacaggcgcc  7980
gataggtgct acgacctaag tttaggactg ccggctgacg ccggcaggtt cgacttggtc  8040
tttgtgaaca ttcacacgga attcagaatc caccactacc agcagtgtgt cgaccacgcc  8100
atgaagctgc agatgcttgg gggagatgcg ctacgactgc taaaacccgg cggcagcctc  8160
ttgatgagag cttacggata cgccgataaa atcagcgaag ccgttgtttc ctccttaagc  8220
agaaagttct cgtctgcaag agtgttgcgc ccggattgtg tcaccagcaa tacagaagtg  8280
ttcttgctgt tctccaactt tgacaacgga aagagaccct ctacgctaca ccagatgaat  8340
accaagctga gtgccgtgta tgccggagaa gccatgcaca cggccgggtg tgcaccatcc  8400
tacagagtta agagagcaga catagccacg tgcacagaag cggctgtggt taacgcagct  8460
aacgcccgtg gaactgtagg ggatggcgta tgcagggccg tggcgaagaa atggccgtca  8520
gcctttaagg gagaagcaac accagtgggc acaattaaaa cagtcatgtg cggctcgtac  8580
cccgtcatcc acgctgtagc gcctaatttc tctgccacga ctgaagcgga aggggaccgc  8640
gaattggccg ctgtctaccg ggcagtggcc gccgaagtaa acagactgtc actgagcagc  8700
gtagccatcc cgctgctgtc cacaggagtg ttcagcggcg gaagagatag gctgcagcaa  8760
tccctcaacc atctattcac agcaatggac gccacggacg ctgacgtgac catctactgc  8820
agagacaaaa gttgggagaa gaaaatccag gaagccatag acacgaggac ggctgtggag  8880
ttgctcaatg atgacgtgga gctgaccaca gacttggtga gagtgcaccc ggacagcagc  8940
ctggtgggtc gtaagggcta cagtaccact gacgggtcg tgtactcgta ctttgaaggt   9000
acgaaattca accaggctgc tattgatatg gcagagatac tgacgttgtg gcccagactg  9060
caagaggcaa cgaacagat atgcctatac gcgctgggcg aaacaatgga caacatcaga   9120
tccaaatgtc cggtgaacga ttccgattca tcaacacctc ccaggacagt gccctgcctg  9180
tgccgctacg caatgacagc agaacggatc cccgcccta ggtcacacca agttaaaagc   9240
atggtggttt gctcatcttt tccctcccg aaatacatg tagatggggt gcagaaggta    9300
aagtgcgaga aggttctcct gttcgacccg acggtacctt cagtggttag tccgcggaag  9360
tatgccgcat ctacgacgga ccactcagat cggtcgttac gagggtttga cttggactgg  9420
accaccgact cgtcttccac tgccagcgat accatgtcgc tacccagttt gcagtcgtgt  9480
```

```
gacatcgact cgatctacga gccaatggct cccatagtag tgacggctga cgtacaccct   9540
gaacccgcag gcatcgcgga cctggcggca gatgtgcatc ctgaacccgc agaccatgtg   9600
gacctcgaga acccgattcc tccaccgcgc ccgaagagag ctgcatacct tgcctcccgc   9660
gcggcggagc gaccggtgcc ggcgccgaga aagccgacgc ctgccccaag gactgcgttt   9720
aggaacaagc tgcctttgac gttcggcgac tttgacgagc acgaggtcga tgcgttggcc   9780
tccgggatta ctttcggaga cttcgacgac gtcctgcgac taggccgcgc gggtgcatat   9840
attttctcct cggacactgg cagcggacat ttacaacaaa aatccgttag gcagcacaat   9900
ctccagtgcg cacaactgga tgcggtcgag gaggagaaaa tgtacccgcc aaaattggat   9960
actgagaggg agaagctgtt gctgctgaaa atgcagatgc acccatcgga ggctaataag  10020
agtcgatacc agtctcgcaa agtggagaac atgaaagcca cggtggtgga caggctcaca  10080
tcgggggcca gattgtacac gggagcggac gtaggccgca taccaacata cgcggttcgg  10140 taccccccgcc ccgtgtactc ccctaccgtg atcgaaagat tctcaagccc cgatgtagca  10200
atcgcagcgt gcaacgaata cctatccaga aattacccaa cagtggcgtc gtaccagata  10260
acagatgaat acgacgcata cttggacatg gttgacgggt cggatagttg cttggacaga  10320
gcgacattct gcccggcgaa gctccggtgc tacccgaaac atcatgcgta ccaccagccg  10380
actgtacgca gtgccgtccc gtcaccctt cagaacacac tacagagcgt gctagcggcc  10440
gccaccaaga gaaactgcaa cgtcacgcaa atgcgagaac tacccaccat ggactcggca  10500
gtgttcaacg tggagtgctt caagcgctat gcctgctccg gagaatattg ggaagaatat  10560
gctaaacaac ctatccggat aaccactgag aacatcacta cctatgtgac caaattgaaa  10620
ggcccgaaag ctgctgcctt gttcgctaag acccacaact tggttccgct gcaggaggtt  10680
cccatggaca gattcacggt cgacatgaaa cgagatgtca aagtcactcc agggacgaaa  10740
cacacagagg aaagacccaa agtccaggta attcaagcag cggagccatt ggcgaccgct  10800
tacctgtgcg gcatccacag ggaattagta aggagactaa atgctgtgtt acgccctaac  10860
gtgcacacat tgtttgatat gtcggccgaa gactttgacg cgatcatcgc ctctcacttc  10920
cacccaggag acccggttct agagacggac attgcatcat cgacaaaaag ccaggacgac  10980
tccttggctc ttacaggttt aatgatcctc gaagatctag gggtggatca gtacctgctg  11040
gacttgatcg aggcagcctt tgggaaaata tccagctgtc acctaccaac tggcacgcgc  11100
ttcaagttcg gagctatgat gaaatcgggc atgtttctga ctttgtttat taacactgtt  11160
ttgaacatca ccatagcaag cagggtactg gagcagagac tcactgactc cgcctgtgcg  11220
gccttcatcg gcgacgacaa catcgttcac ggagtgatct ccgacaagct gatggcggag  11280
aggtgcgcgt cgtgggtcaa catggaggtg aagatcattg acgctgtcat gggcgaaaaa  11340 ccccccatatt tttgtggggg attcatagtt tttgacagcg tcacacagac cgcctgccgt  11400
gtttcagacc cacttaagcg cctgttcaag ttgggtaagc cgctaacagc tgaagacaag  11460
caggacgaag acaggcgacg agcactgagt gacgaggtta gcaagtggtt ccggacaggc  11520
ttgggggccg aactggaggt ggcactaaca tctaggtata aggtagaggg ctgcaaaagt  11580
atcctcatag ccatggccac cttggcgagg acattaagg cgtttaagaa attgagagga  11640
cctgttatac acctctacgg cggtcctaga ttggtgcgtt aatacacaga attctgattg  11700
gatcctcgag gaattctgac actatgaagt gccttttgta cttagccttt ttattcattg  11760
gggtgaattc caagttcacc atagtttttc cacacaacca aaaaggaaac tggaaaaatg  11820
ttccttctaa ttaccattat tgcccgtcaa gctcagattt aaattggcat gatgacttaa  11880
```

```
taggcacagc cttacaagtc aaaatgccca agagtcacaa ggctattcaa gcagacggtt    11940
ggatgtgtca tgcttccaaa tgggtcacta cttgtgactt ccgctggtat ggaccgaagt    12000
atataacaca ttccatccga tccttcactc catctgtaga acaatgcaag gaaagcattg    12060
aacaaacgaa acaaggaact tggctgaatc caggcttccc tcctcaaagt tgtggatatg    12120
caactgtgac ggatgccgaa gcagtgattg tccaggtgac tcctcaccat gtgctggttg    12180
atgaatacac aggagaatgg gttgattcac agttcatcaa cggaaaatgc agcaattaca    12240
tatgccccac tgtccataac tctacaacct ggcattctga ctataaggtc aaagggctat    12300
gtgattctaa cctcatttcc atggacatca ccttcttctc agaggacgga gagctatcat    12360
ccctgggaaa ggagggcaca gggttcagaa gtaactactt tgcttatgaa actggaggca    12420
aggcctgcaa aatgcaatac tgcaagcatt ggggagtcag actcccatca ggtgtctggt    12480
tcgagatggc tgataaggat ctctttgctg cagccagatt ccctgaatgc ccagaagggt    12540
caagtatctc tgctccatct cagacctcag tggatgtaag tctaattcag gacgttgaga    12600
ggatcttgga ttattccctc tgccaagaaa cctggagcaa aatcagagcg ggtcttccaa    12660
tctctccagt ggatctcagc tatcttgctc ctaaaaaccc aggaaccggt cctgctttca    12720
ccataatcaa tggtacccta aaatactttg agaccagata catcagagtc gatattgctg    12780
ctccaatcct ctcaagaatg gtcggaatga tcagtggaac taccacagaa agggaactgt    12840
gggatgactg ggcaccatat gaagacgtgg aaattggacc caatggagtt ctgaggacca    12900
gttcaggata taagtttcct ttatacatga ttggacatgg tatgttggac tccgatcttc    12960
atcttagctc aaaggctcag gtgttcgaac atcctcacat tcaagacgct gcttcgcaac    13020
ttcctgatga tgagagttta tttttggtg atactgggct atccaaaaat ccaatcgagc    13080
ttgtagaagg ttggttcagt agttggaaaa gctctattgc ctctttttc tttatcatag    13140 ggttaatcat tggactattc ttggttctcc gagttggtat ccatctttgc attaaattaa    13200
agcacaccaa gaaaagacag atttatacag acatagagat gaaccgactt ggaaagtaac    13260
tcaaatcctg cacaacagat tcttcatgtt tggaccaaat caacttgtga taccatgctc    13320
aaagaggcct caaaccataa ctgtataact tgtaacaaag cgcaacaaga cctgcgcaat    13380
tggccccgtg gtccgcctca cggaaactcg gggcaactca tattgacaca ttaattggca    13440
ataattggaa gcttacataa gcttaattcg acgaataatt ggattttat tttattttgc    13500 aattggtttt taatatttcc aaaaaaaaaa aaaaaaaaaa aaaaaaaaaa aaaaaaaaaa    13560
aaaaaaaaaa aaaaaaaaaa aaaaaaaaaa                                    13590

<210> SEQ ID NO 2
<211> LENGTH: 18
<212> TYPE: PRT
<213> ORGANISM: Thosea asigna virus

<400> SEQUENCE: 2

Glu Gly Arg Gly Ser Leu Leu Thr Cys Gly Asp Val Glu Glu Asn Pro
1               5                   10                  15

Gly Pro
```